(12) United States Patent
Shield et al.

(10) Patent No.: US 11,850,050 B2
(45) Date of Patent: Dec. 26, 2023

(54) APPARATUS AND METHOD FOR KNEE FLEXOR ASSESSMENT

(75) Inventors: Anthony James Shield, Everton Park (AU); David Andrew Opar, Kelvin Grove (AU)

(73) Assignee: QUEENSLAND UNIVSERITY OF TECHNOLOGY, Brisbane (AU)

( * ) Notice: Subject to any disclaimer, the term of this patent is extended or adjusted under 35 U.S.C. 154(b) by 0 days.

(21) Appl. No.: 14/424,577

(22) PCT Filed: Sep. 3, 2012

(86) PCT No.: PCT/AU2012/001041
§ 371 (c)(1),
(2), (4) Date: Jun. 15, 2015

(87) PCT Pub. No.: WO2014/032072
PCT Pub. Date: Mar. 6, 2014

(65) Prior Publication Data
US 2015/0297128 A1    Oct. 22, 2015

(51) Int. Cl.
*A61B 5/22* (2006.01)
*A61B 5/00* (2006.01)
(Continued)

(52) U.S. Cl.
CPC ............ *A61B 5/224* (2013.01); *A61B 5/1107* (2013.01); *A61B 5/30* (2021.01); *A61B 5/4533* (2013.01); *A61B 5/4585* (2013.01); *A63B 21/0023* (2013.01); *A63B 21/00069* (2013.01); *A63B 21/0442* (2013.01); *A63B 21/4013* (2015.10); *A63B 21/4015* (2015.10);
(Continued)

(58) Field of Classification Search
None
See application file for complete search history.

(56) References Cited

U.S. PATENT DOCUMENTS 3,285,070 A    11/1966    McDonough
3,374,675 A     3/1968    Keropian
(Continued)

FOREIGN PATENT DOCUMENTS

CN    201759570 U    3/2011
DE       3609535 A1    9/1987
(Continued)

OTHER PUBLICATIONS

Tom Dang, et al.; "Interactive Video Exercise System for Pediatric Brain Injury Rehabilitation"; Proceedings of the RESNA 20th Annual Conference, Jun. 1998; 3 pages. (Year: 1998).*
(Continued)

*Primary Examiner* — Matthew Kremer
(74) *Attorney, Agent, or Firm* — TAROLLI, SUNDHEIM, COVELL & TUMMINO L.L.P.

(57) ABSTRACT

An apparatus for use in assessing strength of at least one knee flexor muscle of a subject, the apparatus including a support, two securing members, each securing member securing a respective lower leg of the subject in a position that in use is substantially fixed relative to the support and at least one sensor, which in use senses a force indicative of the strength of the at least one knee flexor muscle in at least one leg of the subject while the subject performs an eccentric contraction of the at least one knee flexor muscle.

14 Claims, 23 Drawing Sheets

(51) Int. Cl.
  *A63B 23/02* (2006.01)
  *A63B 21/04* (2006.01)
  *A63B 24/00* (2006.01)
  *A63B 21/002* (2006.01)
  *A63B 21/00* (2006.01)
  *A63B 71/06* (2006.01)
  *A61B 5/11* (2006.01)
  *A61B 5/30* (2021.01)

(52) U.S. Cl.
  CPC ...... *A63B 21/4029* (2015.10); *A63B 21/4031* (2015.10); *A63B 21/4037* (2015.10); *A63B 23/0211* (2013.01); *A63B 23/0238* (2013.01); *A63B 24/0087* (2013.01); *A63B 71/0619* (2013.01); *A61B 5/4528* (2013.01); *A61B 5/6828* (2013.01); *A61B 5/702* (2013.01); *A61B 2503/10* (2013.01); *A61B 2505/09* (2013.01); *A61B 2562/14* (2013.01); *A63B 2071/0625* (2013.01); *A63B 2208/0214* (2013.01); *A63B 2208/0247* (2013.01); *A63B 2208/0252* (2013.01); *A63B 2208/0257* (2013.01); *A63B 2208/0261* (2013.01); *A63B 2209/10* (2013.01); *A63B 2220/40* (2013.01); *A63B 2220/51* (2013.01); *A63B 2220/54* (2013.01); *A63B 2220/58* (2013.01); *A63B 2220/80* (2013.01); *A63B 2220/803* (2013.01); *A63B 2220/805* (2013.01); *A63B 2220/833* (2013.01); *A63B 2220/836* (2013.01); *A63B 2225/09* (2013.01); *A63B 2225/20* (2013.01); *A63B 2225/50* (2013.01); *A63B 2225/54* (2013.01); *A63B 2225/74* (2020.08)

(56) References Cited

U.S. PATENT DOCUMENTS

| | | | | |
|---|---|---|---|---|
| 4,702,108 A | * | 10/1987 | Amundsen | A61B 5/224 482/134 |
| 4,732,038 A | | 3/1988 | DelGiorno et al. | |
| 4,889,108 A | | 12/1989 | Bond et al. | |
| 5,100,130 A | * | 3/1992 | Shoebrooks | A63B 21/4039 482/121 |
| 5,209,712 A | * | 5/1993 | Ferri | A61H 1/02 482/131 |
| 5,662,591 A | * | 9/1997 | Peindl | A61B 5/224 5/648 |
| 6,220,994 B1 | * | 4/2001 | Rich | A63B 21/0004 482/123 |
| 7,770,965 B2 | * | 8/2010 | Zwezdaryk | A47C 15/008 128/845 |
| 2002/0091039 A1 | | 7/2002 | Reinbold et al. | |
| 2004/0110602 A1 | | 6/2004 | Feldman | |
| 2005/0250994 A1 | * | 11/2005 | Krullaards | A61B 5/6887 600/300 |
| 2006/0052220 A1 | * | 3/2006 | Jackson | A63B 21/04 482/52 |
| 2008/0058172 A1 | * | 3/2008 | Tyree | A63B 23/0494 482/92 |
| 2010/0125027 A1 | | 5/2010 | Abiemo | |
| 2013/0072822 A1 | * | 3/2013 | Auchinleck | A61B 5/1036 600/595 |

FOREIGN PATENT DOCUMENTS

| | | | |
|---|---|---|---|
| JP | 2006-346402 A | 12/2006 | |
| JP | 2007-267766 A | 10/2007 | |
| KR | 101009710 B1 | 1/2011 | |
| RU | 2240749 C1 | 11/2004 | |
| WO | WO 03/094732 | 11/2003 | |
| WO | WO-2004107976 A1 | * 12/2004 | ............. A61B 5/224 |
| WO | 2011142537 | 11/2011 | |

OTHER PUBLICATIONS

International Search Report for International Application No. PCT/AU2012/001041 dated Jan. 4, 2013 (4 pages).
Australian Search Information Statement for International Application No. PCT/AU2012/001041 dated Jan. 4, 2013 (1 page).
Arnason et al. "Prevention of hamstring strains in elite soccer: an intervention study." *Scand J. Med. Sci. Sports.* 18:40-48 (2008).
International Preliminary Report on Patentability including Written Opinion for International Application No. PCT/AU2012/001041 dated Jan. 4, 2013 (5 pages).

\* cited by examiner

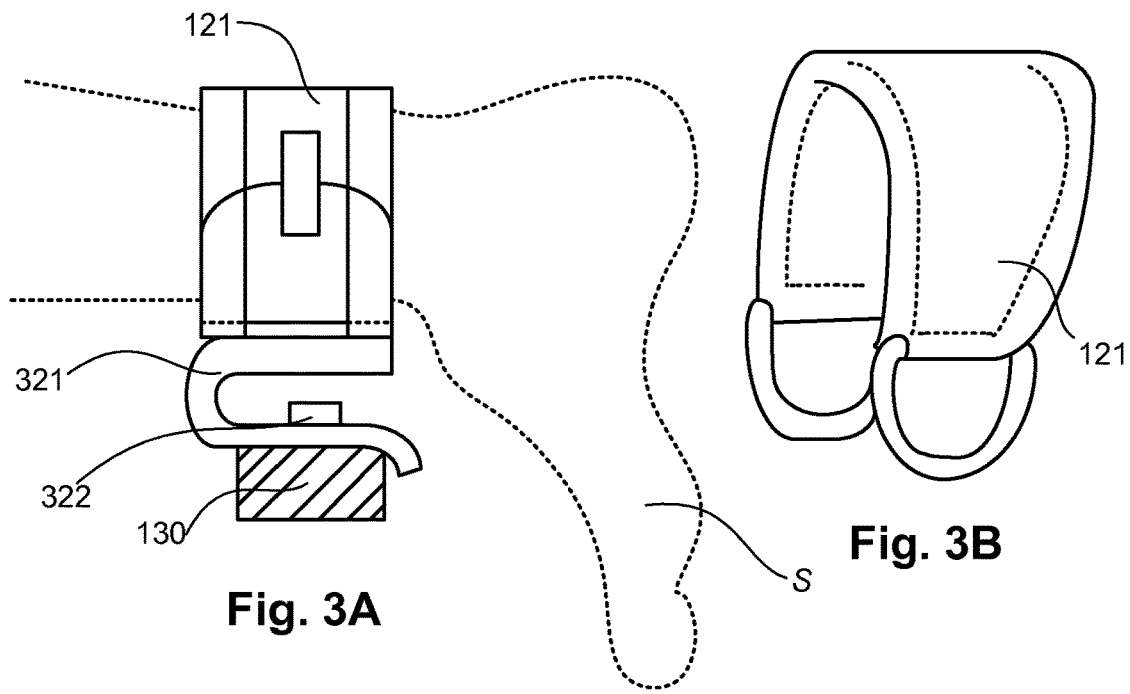
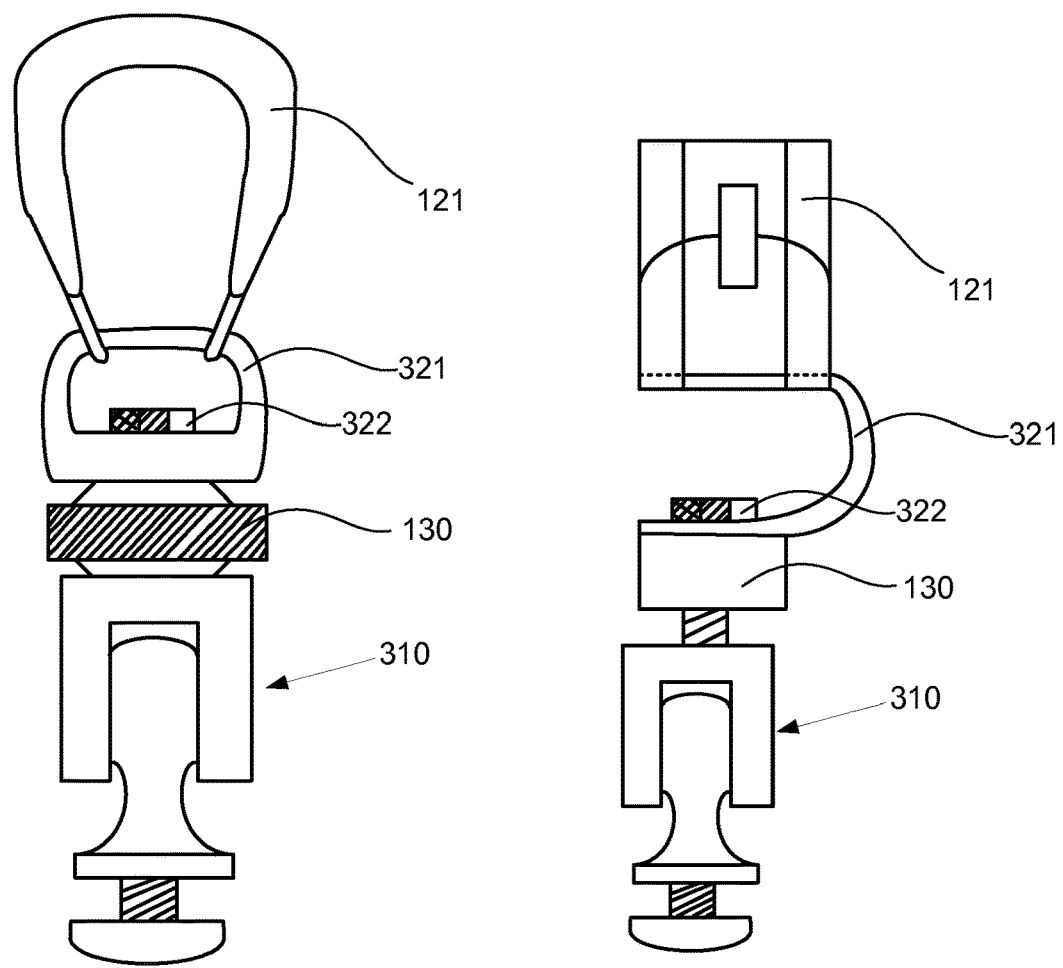

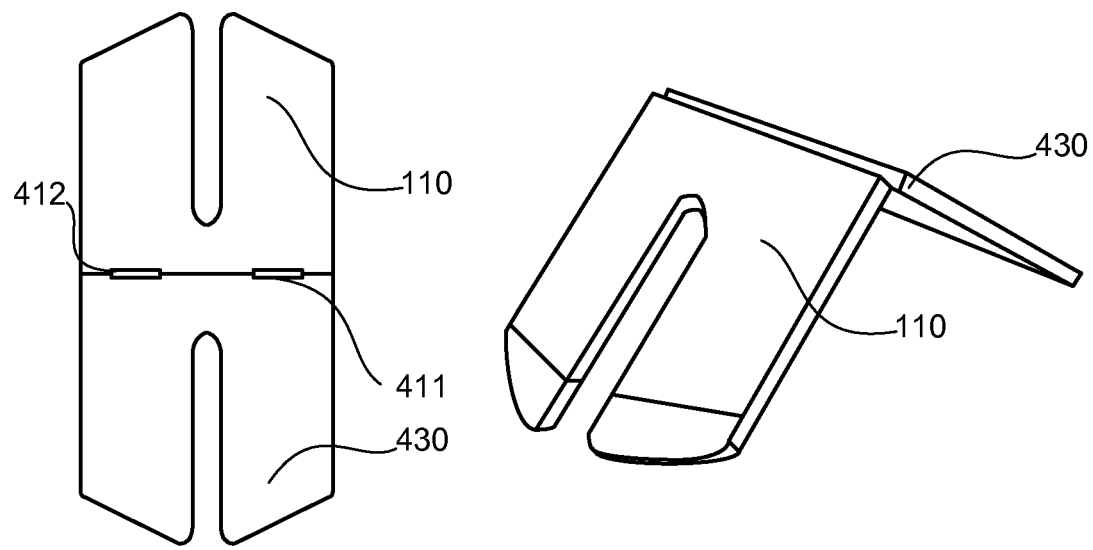
Fig. 6A
Fig. 6B
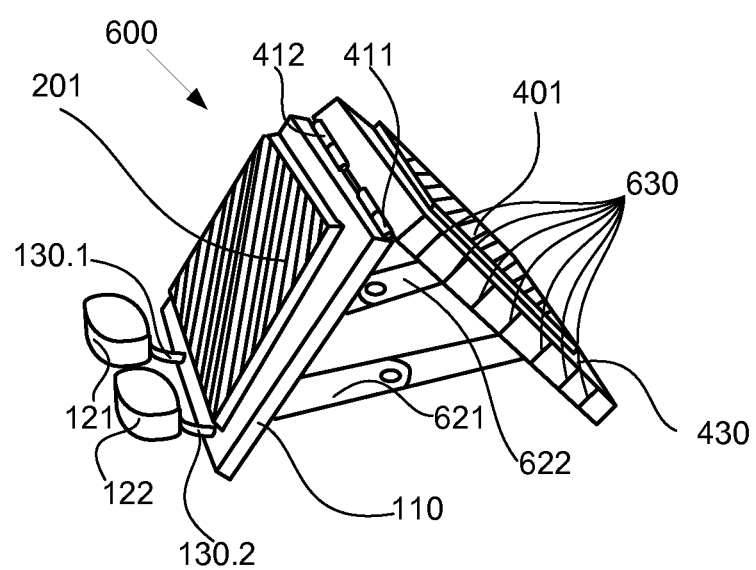
Fig. 6C

APPARATUS AND METHOD FOR KNEE FLEXOR ASSESSMENT

This application is a National Stage Application of PCT/AU2012/001041, filed 3 Sep. 2012 and which application is incorporated herein by reference. To the extent appropriate, a claim of priority is made to the above disclosed application.

BACKGROUND OF THE INVENTION

The present invention relates to an apparatus for use in assessing the strength of at least one knee flexor muscle of a subject, and in one example, for assessing at least the hamstring strength in at least one leg of the subject while the subject performs an eccentric knee flexor contraction.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Hamstring strain injuries (HSIs) are common in both amateur and elite participants in a number of sports including sprinting, athletics, soccer, and other types of football. Furthermore, following an initial HSI, the rate of reoccurrence in a subject is high, with the period of recovery increasing following subsequent HSIs.

Numerous investigations have been conducted into the factors that influence a subject's susceptibility to HSI, as well as circumstances which aid a subject's recovery and decrease instances of reoccurrence. Studies such as Amason et al. 'Prevention of hamstring strains in elite soccer: an intervention study' (2008) 18 *Scand J Med Sci Sports* theorise that increased eccentric hamstring strength correlates with a lower incidence of HSI. Similarly, WO-03/094732 suggests that repeated periods of eccentric exercise of the hamstring can decrease a subject's susceptibility to HSI, and in this respect WO-03/094732 provides an example apparatus for performing eccentric exercises including a padded board and ankle straps.

Despite the conclusions drawn by these studies, existing methods and apparatus for quantitatively assessing knee flexor muscle strength, such as hamstring strength are not widely used, due to a number of inherent limitations. For example, the current gold standard apparatus for performing hamstring strength assessment is a typically laboratory based isokinetic dynamometer. During assessment, a subject is seated, or prone, with an ankle secured to a rotatable arm such that the torque applied by the leg upon rotating the arm is sensed, while the maximum velocity of rotation is constrained by the dynamometer. Isokinetic dynamometers are, however, expensive, require experienced operators, have limited portability, and require significant time to assess each leg of a subject independently. Thus they are largely used for research purposes and only occasionally by elite athletes or sporting teams to assess players at a higher risk of HSI, or to monitor rehabilitation progress. Furthermore, there is a perception among some sporting support personnel that isokinetic dynamometry itself poses an injury risk.

WO-03/094732 describes apparatus for evaluating the susceptibility of a muscle to damage during eccentric contraction including a torque measuring device for obtaining measurements of torque generated by the muscle at different angles of extension. A computer connected to the torque measuring device receives and processes the measurements of torque and evaluates the susceptibility to damage using computer software. The computer software includes a data receiving component for receiving measurements for torque generated by the muscle at different angles of extension, a comparison data component for storing comparison data representative of expected measurements for torque which would be.generated if the muscle were not susceptible to damage during eccentric contraction and an evaluation component for comparing the received measurements with the comparison data to identify differences in torque measurements at the same angles of extension.

U.S. Pat. No. 5,662,591 teaches an apparatus for measuring the strength of and for performing physical therapy exercises to strengthen a patient's limb. The device includes a pair of pivot clamps each having an end for connecting the pivot clamps to a solid object such as a physical therapy table or hospital bed. A second end of each pivot clamp adjustably receives a first frame member of a conventional traction or load frame. This arrangement enables rotational and translational movement of the first frame member retained by the pivot clamp relative to each pivot clamp to allow the frame to be positioned in a desired location and orientation relative to the patient's limb to be tested. A second frame member is adjustably connected to the pair of first frame members by a pair of adjustable brackets. A limb engaging member having a force transducer located therein is used to both engage the patient's limb to be tested and to detect a force transmitted between the limb of a patient and the limb engaging member. The force transducer produces an output which is representative of the force produced which may be displayed on a digital panel meter.

In U.S. Pat. No. 3,285,070 the invention relates, to apparatus adapted for use in a program of physical development and/or rehabilitation. More particularly, the invention relates to apparatus for evaluating and increasing the strength of various muscles and muscle sets of the human body.

In U.S. Pat. No. 3,374,675 the invention relates to ergometer devices or isometric muscle testing apparatus and more particularly to such devices in which muscular strength of physical movement may be tested between an initial joint of movement of a body member and the extremity or at least another spaced portion of the body member, the muscles of which are being tested. Such testing in the human body is sometimes referred to as isometric muscle testing, and two examples of its most general use are in testing muscles in practice of physical therapy, and in physical exercising procedures.

U.S. Pat. No. 4,889,108 describes a muscle exercise and diagnostic system which includes a lever arm, a mounting arrangement for mounting the lever arm for rotation about a fixed axis, and a connecting arrangement for connecting a selected portion of the human body to the lever arm for rotation about a selected anatomical axis of rotation. The connecting arrangement provides a fixed tangential and sliding mounting to permit free radial movement of the point of attachment of the patient relative to the axis of rotation of the lever arm. A velocity control arrangement coupled to the lever arm limits the velocity in accordance with a preselected velocity control function. The radial distance from the point of attachment to the axis of rotation is measured and used in the velocity control function. Range of motion limits are set in one embodiment by way of a potentiometer for each limit position and by a pushbutton and limit storing arrangement in another embodiment.

U.S. Pat. No. 4,909,262 teaches an apparatus utilizing a clamp mechanism for holding a rotating body limp. A mechanical arm is linked to the clamp mechanism and rotatably connects to a pivot member. The angular rotation of the mechanical arm about the pivot member is measured simultaneously with force exerted by the rotating body limb on the clamp mechanism. A strain gauge is linked to the clamp mechanism to provide such force measurement.

It will be appreciated that the abovementioned disclosures suffer from a number of disadvantages including a substantial size or weight which impedes portability, and, significant assessment times that preclude mass screenings, for example, of entire sporting teams. Furthermore, previous methods and apparatus have failed to provide simultaneous assessment of hamstring strength in both legs, independently, during a bilateral exercise, or a combined assessment of hamstring strength in both legs during a bilateral exercise. Additionally existing techniques have questionable reliability and repeatability of measurements of between limb strength imbalances.

SUMMARY OF THE PRESENT INVENTION

The present invention seeks to ameliorate one or more of the problems associated with the prior art.

In a first broad form the present invention seeks to provide an apparatus for use in assessing strength of at least one knee flexor muscle of a subject, the apparatus including:
 a) a support;
 b) two securing members, each securing member securing a respective lower leg of the subject in a position that in use is substantially fixed relative to the support; and,
 c) at least one sensor, which in use senses a force indicative of the strength of the at least one knee flexor muscle in at least one leg of the subject while the subject performs an eccentric contraction of the at least one knee flexor muscle.

Typically the at least one sensor is coupled to at least one of the two securing members, and wherein the sensor senses a force exerted at an lower leg of the subject.

Typically the at least one sensor includes two sensors, each sensor being coupled to a respective securing member to thereby sense the force indicative of the strength of the at least one knee flexor muscle in each leg of the subject.

Typically in use the sensors sense the force indicative of the strength of the at least one knee flexor muscle in each leg of the subject simultaneously.

Typically in use the sensors sense the force indicative of the strength of the at least one knee flexor muscle in each leg of the subject at different times.

Typically at least one securing member is attached to the sensor.

Typically the securing members are coupled to the support.

Typically the securing members are movably mounted to the support

Typically the support includes at least one knee support that in use supports at least one knee of the subject.

Typically the knee support is movably mounted to the support.

Typically the apparatus includes an electronic processing device for:
 a) monitoring signals from the at least one sensor; and,
 b) generating at least in part using the signals an indicator indicative of the hamstring strength for at least the hamstring.

Typically the indicator is indicative of at least one of:
 a) an instantaneous force;
 b) a rate of force development;
 c) an average force;
 d) a peak force;
 e) an impulse;
 f) work;
 g) an instantaneous torque;
 h) a rate of torque development;
 i) an average torque;
 j) changes in force over time;
 k) changes in torque over time; and
 l) a peak torque.

Typically the electronic processing device is for:
 a) comparing the signals at least in part, and reference data; and
 b) generating the indicator in accordance with the results of the comparison.

Typically the reference data includes at least one of:
 a) a tolerance determined from a normal population;
 b) a predetermined range;
 c) a predetermined reference;
 d) a previously generated indicator; and,
 e) an indicator generated for another leg.

Typically the indicator is indicative of:
 a) the signals at least in part, and the reference data; and
 b) a difference between the signals at least in part, and the reference data.

Typically the apparatus includes an output for presenting at least the indicator to the user.

Typically the output is at least one of:
 a) an light emitting diode (LED);
 b) a sound emitting member;
 c) a digital display; and
 d) an electronic signal emitting member.

Typically the output generates at least one of:
 a) a light;
 b) a sound;
 c) at least one alphanumeric character;
 d) a graph;
 e) a picture;
 f) a wireless electronic signal; and
 g) a wired electronic signal.

Typically the apparatus includes an input, thereby allowing a user to input data.

Typically the input includes at least one of:
 a) a keypad;
 b) a keyboard;
 c) a touch screen;
 d) a button; and,
 e) a switch.

Typically the support is elongated and wherein the securing members are provided at a first end, and a second end supports a weight of the subject.

Typically the sensor includes any one of:
 a) a load cell;
 b) a force plate;
 c) a piezoresistive force sensor;
 d) a strain gauge; and
 e) an hydraulic pressure gauge.

Typically the sensor senses any one of a compression force and a tensile force.

Typically the securing members include any one of the following:
a) a strap;
b) a cuff; and,
c) a tie.

Typically the sensor senses a force indicative of the hamstring strength in at least one leg of the subject while the subject performs a Nordic hamstring exercise.

Typically the at least one knee flexor, muscle includes at least a hamstring muscle.

In a second broad form the present invention seeks to provide an apparatus for use in assessing muscle strength of a subject, the apparatus including:
a) a support;
b) two securing members, each securing member constraining movement of a respective lower leg of the subject relative to the support; and,
c) at least one sensor, which in use senses a force indicative of the muscle strength while the subject performs an exercise of the muscle, the exercise exerting at least some force on the sensor.

In a third broad form the present invention seeks to provide a method of assessing hamstring strength of a subject using an apparatus including a support, two securing members, and at least one sensor, the method including:
a) securing two lower legs of a subject using the respective securing members, at a position that is in use substantially fixed relative to the support;
b) sensing a force indicative of the strength of the at least one knee flexor muscle in at least one leg of the subject using the sensor while the subject performs an eccentric contraction of at least a hamstring.

Typically at least one sensor includes two sensors, each sensor being coupled to a respective securing member, and wherein the method includes sensing the force indicative of the strength of the at least one knee flexor muscle in each leg of the subject.

Typically the method includes sensing the force indicative of the strength of the at least one knee flexor muscle in each leg of the subject simultaneously.

Typically the method includes sensing the force indicative of the hamstring strength in at least one leg of the subject while the subject performs a Nordic hamstring exercise.

Typically the method includes an electronic processing device, the method including:
a) monitoring signals from the at least one sensor; and,
b) generating at least in part using the signals an indicator indicative of the hamstring strength for at least the hamstring.

Typically the method includes:
a) comparing the signals at least in part, and reference data; and
b) generating the indicator in accordance with the results of the comparison.

Typically the method includes presenting at least the indicator to the user on an output.

BRIEF DESCRIPTION OF THE DRAWINGS

An example of the present invention will now be described with reference to the accompanying drawings, in which:

FIG. 3A is a schematic diagram of an example of a securing member and sensor;

FIG. 3B is a schematic diagram of a further example of a securing member;

FIGS. 3C to 3F are schematic diagrams of further examples of a securing member and a sensor, including a movable coupling;

FIGS. 6A and 6B are schematic diagrams of a ninth example of an apparatus for use in assessing knee flexor strength of a subject, the apparatus including a hingeably coupled extendable portion;

FIG. 6C is a schematic diagrams of a further example of an apparatus for use in assessing knee flexor strength of a subject, the apparatus including a hingeably coupled extendable portion;

DETAILED DESCRIPTION OF THE PREFERRED EMBODIMENTS

An example of an apparatus for use in assessing strength of at least one knee flexor muscle of a subject will now be described with reference to FIGS. 1A to 1F.

In this example, the apparatus 100 includes a support 110, and two securing members 121, 122, that in use secure a respective lower leg of the, subject S in a position that is substantially fixed relative to the support 110.

The apparatus 100 further includes two sensors 130.1, 130.2 that, in use, sense a force indicative of the strength of at least one knee flexor muscle in one or both legs of the subject S while the subject S performs an eccentric contraction of the at least one knee flexor muscle.

It should be noted that the knee flexor muscles typically include the three major hamstring muscles, semitendinosus, semimembranosus and biceps femoris, as well as the minor knee flexors, sartorius, gastrocnemius, and gracilis. For ease, the following description will refer primarily to measuring the strength of the hamstring. However, it will be appreciated that the techniques can apply to measuring any one or more of the knee flexor muscles and that reference to the hamstring is not intended to be limiting.

Figure 1A:
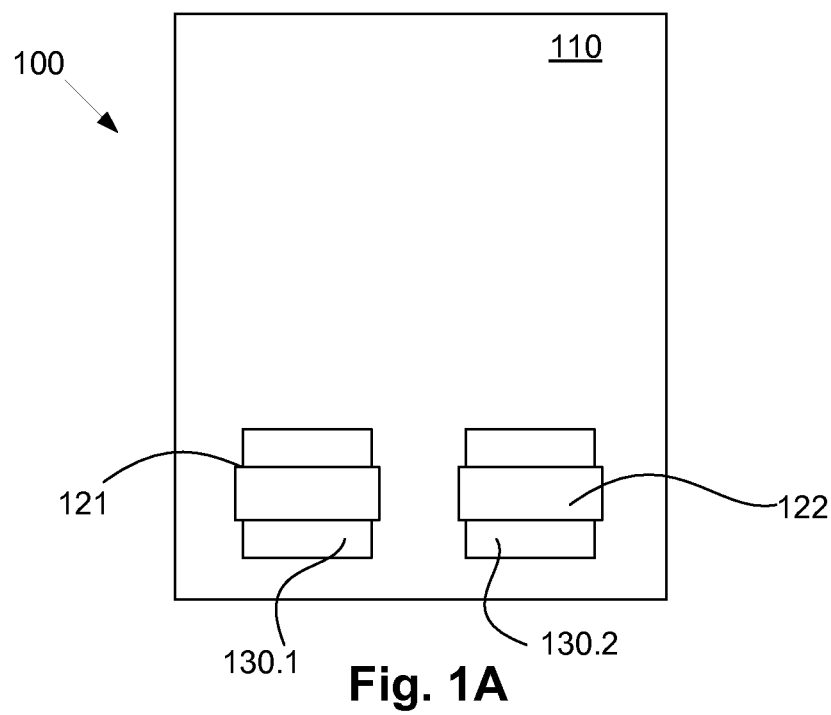
FIGS. 1A to 1C are schematic drawings of a plan, side, and perspective view of a first example of an apparatus for use in assessing knee flexor strength of a subject.
Figure 1B:
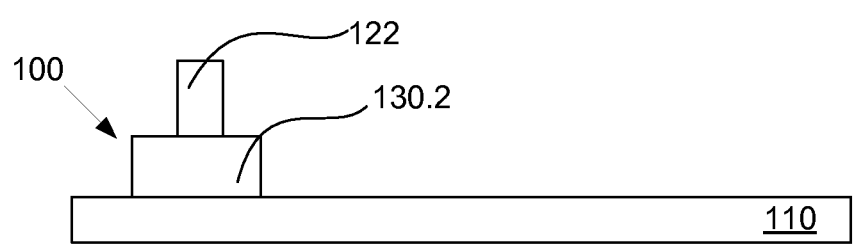
Figure 1C:
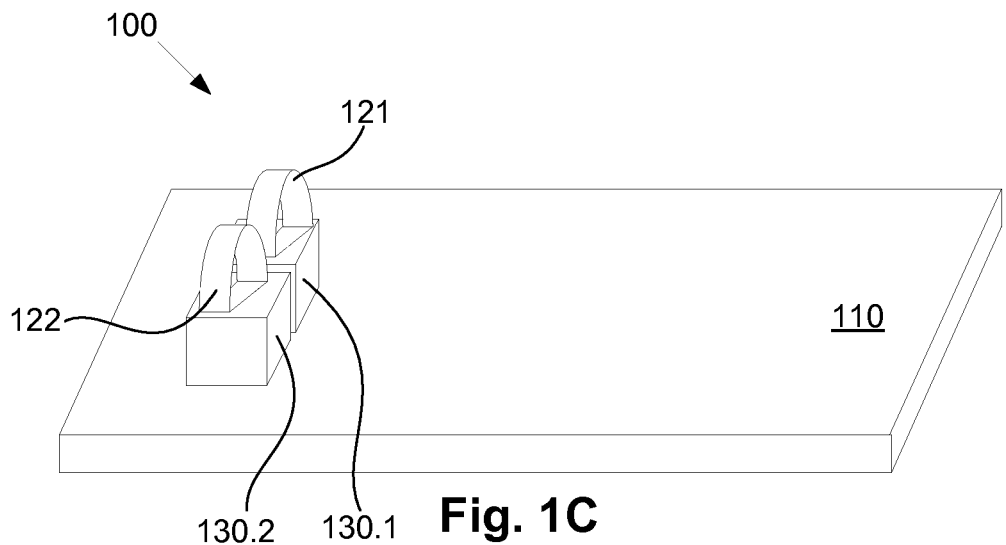
Figure 1D:
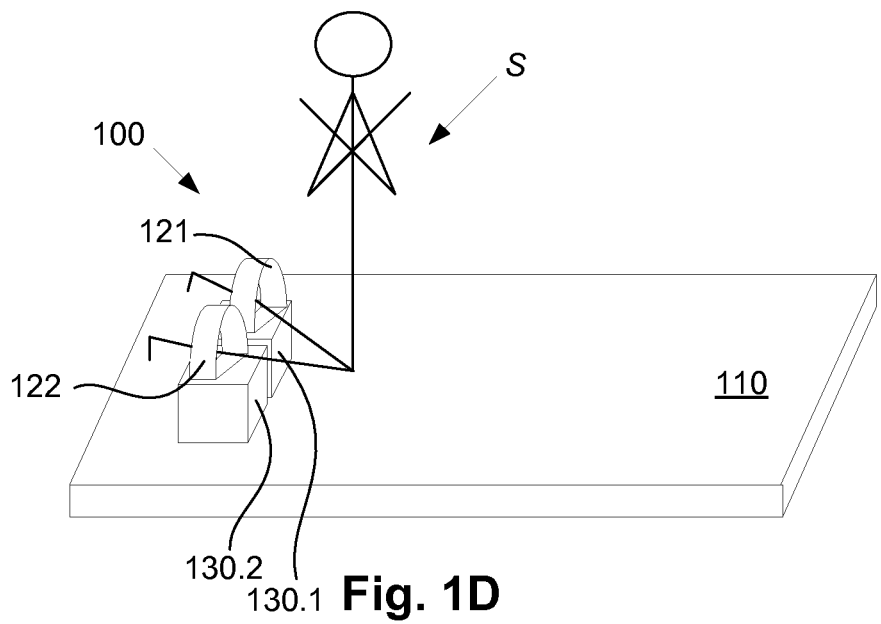
FIGS. 1D to 1F are schematic drawings of a first example of a subject performing an eccentric contraction of at least a knee flexor using the apparatus.
Figure 1E:
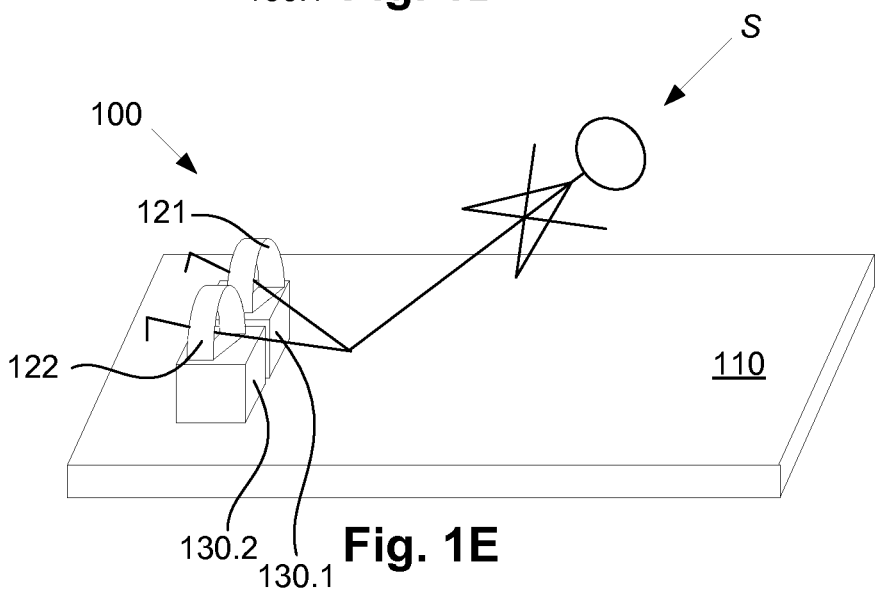
Figure 1F:
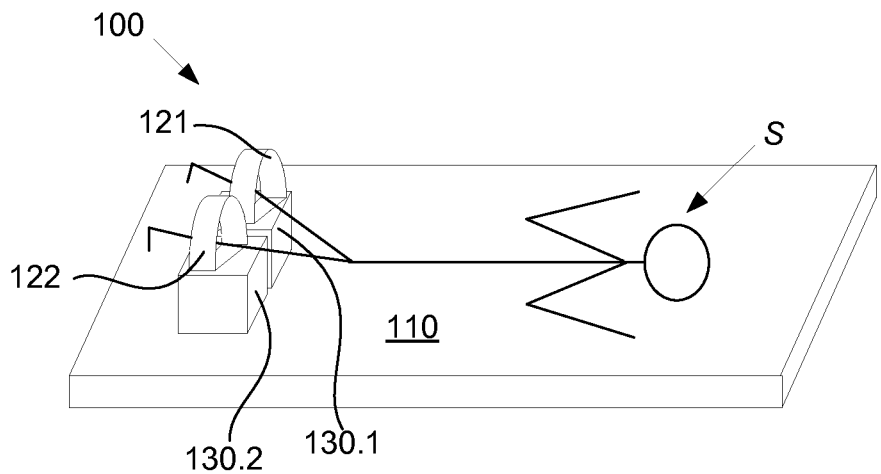

FIGS. 1D to 1F show a subject S performing an eccentric contraction of at least a hamstring using the apparatus 100. In this respect, FIG. 1D shows the subject S in an initial kneeling position prior to commencing the contraction, in which the subject's lower legs are secured using the respective securing members 121, 122 in a position that in use is substantially fixed relative to the support. The subject S subsequently proceeds to lower their upper body toward the support 110 in a controlled manner, while substantially maintaining alignment of the upper legs or thighs and torso, as shown in FIG. 1E. FIG. 1F shows a final position, with the subject S laying substantially prone on the support 110. It will be appreciated that the abovementioned eccentric contraction is typically called the 'Nordic hamstring exercise', 'Nordic curl', or the like.

Accordingly, the above-described arrangement provides apparatus 100 for use in assessing hamstring strength of a subject S, in which the force exerted at the lower leg of the subject S while they perform an eccentric contraction of at least the hamstring is indicative of hamstring strength. In this regard, the apparatus 100 can be utilised to monitor hamstring strength, including any changes in hamstring strength over time, for example, to detect injury precursors such as temporal strength differences, imbalances between legs at rest (i.e. not fatigued) or in response to fatigue, to monitor rehabilitation progress, to monitor progress during strength training, or to benchmark against a population. Additionally or alternatively, the apparatus 100 can also be used in order to strengthen the hamstring, for example, by performing repetitions of an eccentric contraction of the hamstring using the apparatus 100, such as shown in FIGS. 1D to 1F.

Typically, hamstring strength is assessed using a large, typically laboratory-based isokinetic dynamometer, which is expensive and requires highly skilled personnel to oversee the assessment procedure. In contrast, the apparatus 100 can be easily manufactured, thus manufacturing costs remain low resulting in a cost-effective arrangement for assessing hamstring strength. Additionally the apparatus 100 allows non-technical users to easily and effectively use and monitor the apparatus 100.

In addition, the apparatus 100 is portable and may be easily transported. It will be appreciated that portability allows subjects, such as members of a sporting team, to easily transport the apparatus 100 on tour, to/from events, training sessions, or similar, on a team bus, airplane, train, car, or the like. Furthermore, it will be appreciated that the apparatus 100 can also be modularised in order to increase portability. Accordingly, the securing members 121, 122 and/or the one or more sensors 130.1, 130.2 may be provided separately to the support 110 and/or each other and may be easily assembled or disassembled. However this feature is not essential.

It will also be appreciated that the apparatus 100 including two sensors 130.1, 130.2 allows the assessment of the hamstring strength of both hamstrings of a subject S, at the same time. Accordingly the sensors 130.1, 130.2 may sense the force indicative of at least the hamstring strength in each leg of the subject S simultaneously. In this regard, the assessment may be performed in significantly less time than existing methods, for example isokinetic dynamometry, which is limited to assessing hamstrings of opposing legs at different times. The apparatus also appears to provide enhanced sensitivity and reliability for the assessment of between limb strength imbalances compared to existing techniques. This reduces the time required to assess a subject S, which allows the assessment of hamstring strength to become accessible to entire sporting teams as part of regular health and fitness assessments. In this example, two sensors 130.1, 130.2 are shown, however this is not essential and any number of sensors, including a single sensor may be used for monitoring force in one leg, or alternatively a single sensor may be used to monitor the combined hamstring strength of both legs.

In this example, an eccentric contraction of at least the hamstring of a subject S is shown in FIGS. 1D to 1F, however it will be appreciated that any suitable exercise which includes an eccentric contraction of the hamstring may be performed. For example, the subject's hip may be positioned differently, such that the eccentric contraction is performed with the subject's hip and trunk flexed forward. However, this is not essential, and although in this example, the apparatus 100 is for use during an eccentric contraction of at least the hamstring of a subject S, it will be appreciated that the apparatus 100 may be used to measure other muscles or muscles groups while performing other types of muscle contractions. For example, the apparatus 100 may be used to assess any suitable muscle or muscle group, such as the knee flexor, hip flexor, knee extensor, quadriceps, or the like. In this regard, the assessment may be made during an eccentric, isometric, or concentric contraction, or the like, of the respective muscle or muscle group.

In a further example, the apparatus 100 may be used in assessing hamstring strength, while the subject S performs a concentric contraction of at least the hamstring. The concentric contraction of the hamstring may include the subject S being provided in an initial, substantially prone position, for example as shown in FIG. 1F, in which the subject's lower legs are secured using the respective securing members 121, 122 in a position that in use is substantially fixed relative to the support. The subject S subsequently proceeds to raise their upper body toward the support 110 in a controlled manner, while substantially maintaining alignment of the upper legs or thighs and torso, as shown in FIG. 1E. FIG. 1D shows a final position, with the subject S substantially kneeling on the support 110. However, this exercise is not essential, and any suitable exercise may be performed to assess any suitable muscle or muscle group.

Accordingly, the above provides an apparatus 100 for use in assessing muscle strength of a subject S including a support 110, and two securing members 121, 122, for constraining the movement of a respective lower leg of the subject S relative to the support 110. The apparatus 100 further includes one or more sensors 130.1, 130.2, which in use sense a force indicative of the muscle strength while the subject S performs an exercise of the muscle, the exercise exerting at least some force on the sensor 130.1, 130.2.

A number of further features will now be described.

In another example, each sensor 130.1, 130.2 is coupled to a respective securing member 121, 122 that secures the ankles of a subject S relative to the support 110 and accordingly the force sensed at the ankles is indicative of hamstring strength. However, this feature is not essential and it will be appreciated that the sensors 130.1, 130.2 may sense a force exerted at any part of the lower leg, for example under the knees of the subject S.

Furthermore, the assessment of hamstring strength may occur during a unilateral or bilateral contractions of the hamstring/s. For example, during a bilateral contraction, two sensors 130.1, 130.2 may be used to sense the force in each leg of the subject simultaneously or at different times, or alternatively a single sensor 130.1, 130.2 may be used to sense the force in either or both legs. During a unilateral contraction, the apparatus may include one sensor 130.1, 130.2 which is interchangeable between the lower legs of the subject, by repositioning the sensor 130.1, 130.2 and/or the securing members 121, 122 and/or the subject S relative to the support 110, such that the hamstring strength in both legs can be assessed sequentially. However, this feature is not essential.

It will be appreciated that the apparatus 100 may be used for assessing hamstring strength, including assessing between leg imbalance, fatigue (or fatigability), improvement, rehabilitation, benchmarking, or the like, and this will be discussed in more detail below. In addition, the apparatus 100 may be used in conjunction with other diagnostic, experimental or complementary equipment or procedures, for example electromyography (EMG) for assessing the electrical activity in skeletal muscles, or the like, however this is not essential.

Additionally or alternatively, the apparatus 100 may be used for muscle strengthening, for example, by the subject S repeatedly performing the eccentric contraction of at least the hamstring using the apparatus 100.

In one example, the support 110 is elongated and the securing members 121, 122 are provided at a first end, and a second end supports a weight of the subject S. However, this is not essential, and the support 110 can be any suitable shape as discussed in more detail below.

A number of further examples of the support 110 are shown in FIGS. 2A to 2D. Features similar to those of the example apparatus described above have been assigned correspondingly similar reference numerals.

Figure 2A:
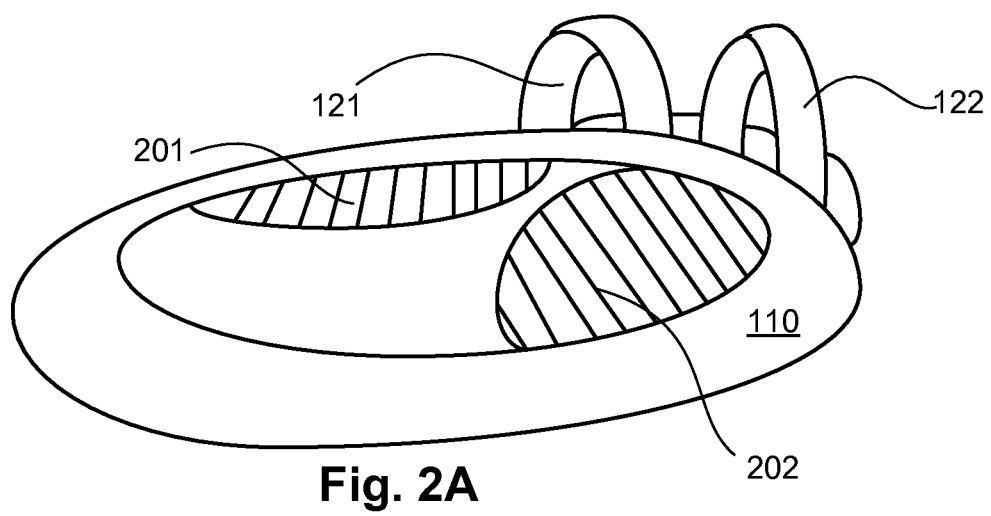
FIGS. 2A to 2E are schematic diagrams of a number of examples of a support.
Figure 2B:
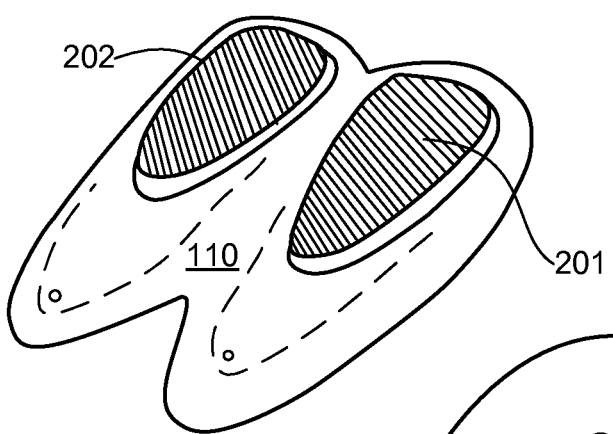
Figure 2C:
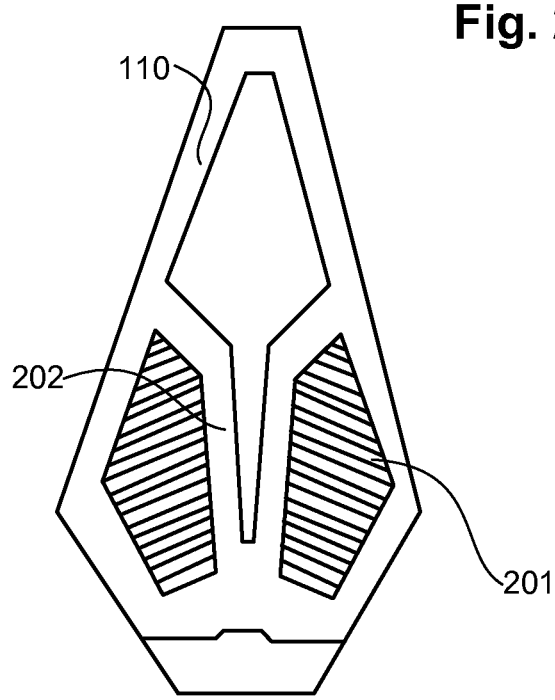
Figure 2D:
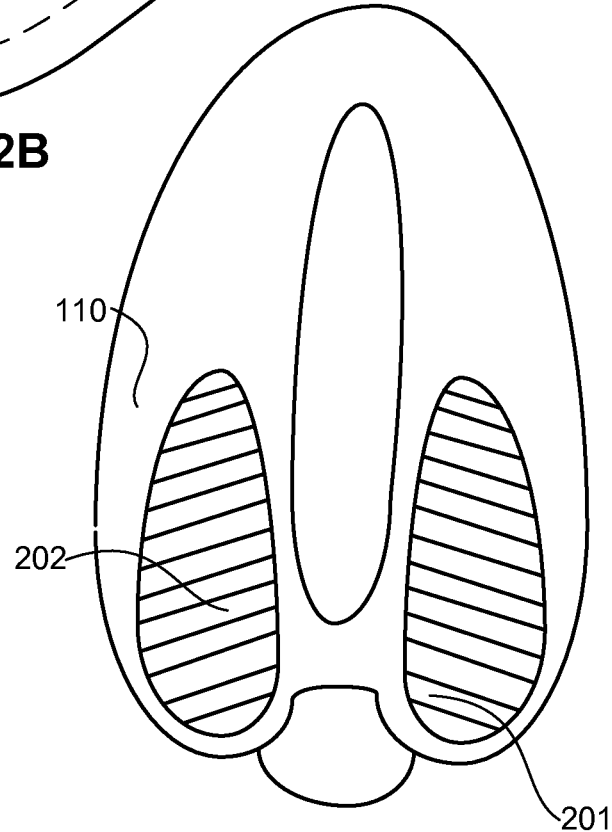

FIGS. 2A to 2E show further examples of a support 110. In FIG. 2A, the support further includes two securing members 121, 122 for securing a respective lower leg of the subject S in a position that is, in use, substantially fixed relative to the support 110. The one or more sensors 130.1, 130.2 are not shown. In FIGS. 2B to 2D, the securing members 121, 122 and one or more sensors 130.1, 130.2 are not shown.

In this regard, the support 110 may include any suitable shape, including oval, circular, polygonal, square, rectangular, ergonomic, or the like. Furthermore, the support 110 may be composed of any suitable material in order to withstand the weight of at least part of the subject S, such as timber, medium density fibreboard (MDF), plastic, fibreglass, carbon fibre reinforced polymer (CFRP), aluminium, or the like.

Figure 2E:
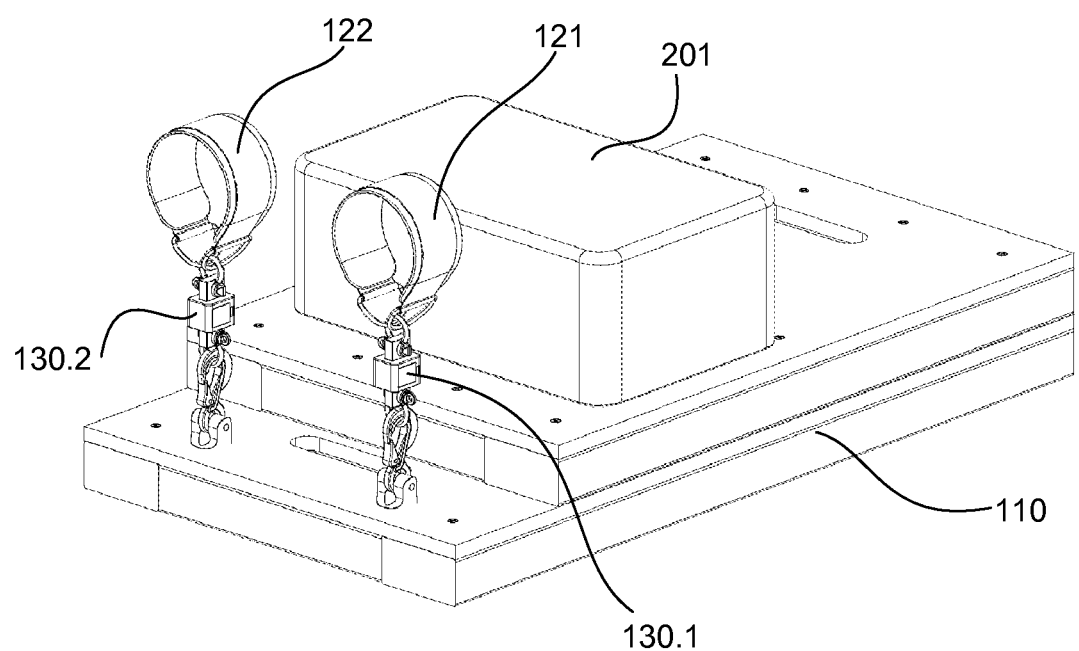

In FIG. 2E, the support 110 includes a stepped profile, such that the knee support 201 is provided on a higher portion of the support 110, and the sensors 130.1, 130.2 are coupled to a lower portion of the support 100. It will be appreciated that this allows the lower legs of the subject S to be arranged substantially parallel to the support 110, when each securing member 121, 122 secures a respective lower leg of the subject S in a position that in use is substantially fixed relative to the support 110. However, this feature is not essential, and the support may include any suitable profile, including a profile that is uniform, graduated, or the like.

It will also be appreciated that whilst a single unitary support is shown, this is for ease of illustration only and that in practice the support could be formed from multiple support members, which may or may not be interconnected. In one example, the support could include two parallel support members, each of which is for coupling to a respective securing member.

In these examples, each support 110 includes one or more knee supports 201, 202 that support one or more knees of the subject S, which in use, protects the subject's knees from injury, damage, pain, or similar. Accordingly, the knee supports 201, 202 may be composed of any suitable material, including foam, rubber, cloth, or the like.

It will be appreciated that the knee supports 201, 202 may be movably mounted to the support 110. Subjects S of different sizes, and in particular of different heights, will exhibit a variance in the distance between their knee and respective lower leg, upon which the securing member 121, 122 is secured. Hence, the knee supports 201, 202 may be movably mounted, for example, to adjust the distance from the securing members 121, 122, the distance between respective knee supports 201, 202, the angle of the knee supports 201, 202, or the like, in order to suit a particular subject S. Accordingly, the movable mounting may include any suitable mounting such as guide rails, semi-rigid mountings, or the like. However, this feature is not essential, and alternatively elite athletes may have bespoke apparatus 100, or the knee supports 201, 202 may be sufficiently sized to accommodate a range of subjects S of different sizes.

A number of further examples of the securing members 121, 122 are shown in FIGS. 3A to 3H. Features similar to those of the example apparatus described above have been assigned correspondingly similar reference numerals.

FIG. 3A shows an example of the securing member 121 coupled to a sensor 130. In this regard, the coupling includes a "C"-shaped member 321 and fastener 322, for example a bolt, screw, nail, or the like, however it will be appreciated that any suitable coupling may be used. Furthermore, the securing member 121 includes a detachable cuff, including a fastening such as Velcro™, buttons, zip, or the like, such that the cuff receives the lower leg of the subject S, however any suitable securing member 121 may be used, as will be discussed in further detail below.

Figure 3E:
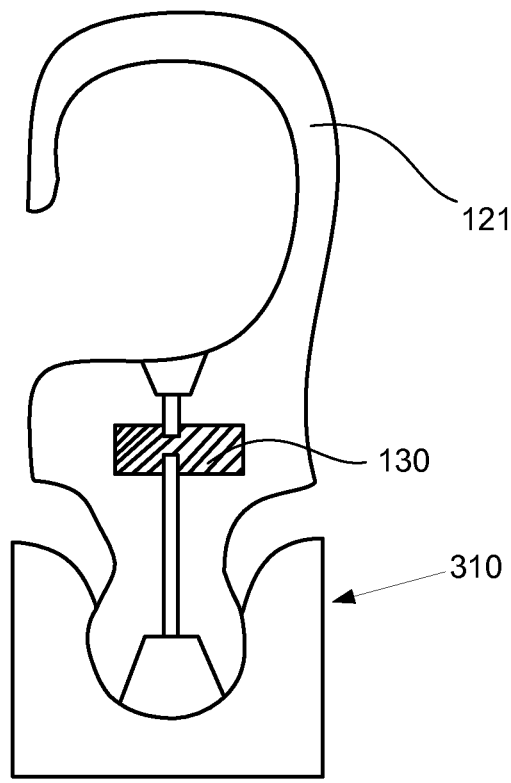

In FIG. 3B, a further example of the securing member 121 is shown, including a flexible and/or arcuate body. It will be appreciated that in this example, the securing member is secured to the sensor 130, as shown in FIG. 3C, using one or more couplings, that in use allow the subject S to place their lower leg directly through the body, and/or require the detachment/attachment of at least one coupling. However, it will be appreciated that this feature is not essential, and any suitable securing member 121 may be used, for example, a cuff, a tie, a strap, a semi-rigid "C" shaped member for example as shown in FIGS. 3E and 3F that allows for ease in securing and unsecuring a lower leg, or the like.

Figure 3F:
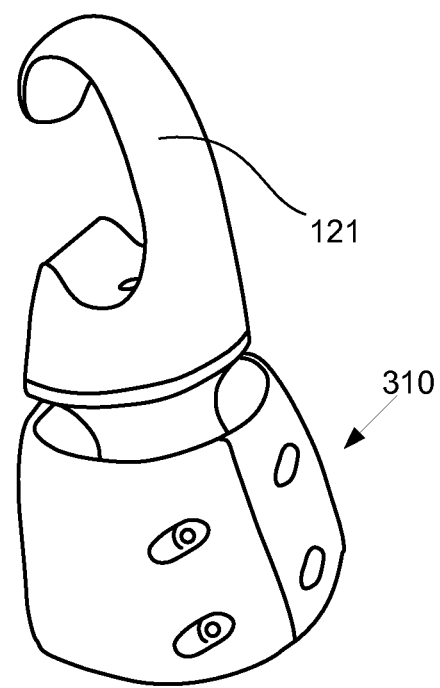

FIGS. 3C to 3F show four examples of a securing member 121, coupled to a sensor 130. It will be appreciated, this may be achieved using any suitable means, including a "D"-shaped member 321, as shown in FIG. 3C, or "C"-shaped member 321, as shown in FIG. 3D and fastener 322. Alternatively, the sensor 130 may be included in the securing member 121, as shown in FIGS. 3E and 3F, or the securing member 121 may be directly coupled to the sensor 130, or coupled via a tie, screw, bolt, adhesive, or the like. It will also be appreciated that the arrangement in FIGS. 3E and 3F may allow the sensor to sense either or both compressive and tensile forces, for example depending on the exercise being performed. However, this feature is not essential.

In these examples, the sensor 130 includes any suitable sensor including a load cell, a force plate, a piezoresistive force sensor, a strain gauge, a hydraulic pressure gauge, or the like. Additionally, the sensor 130 may sense either a compression force or a tensile force, and in this respect the positioning of the sensor 130 will be dependent on the type of force to be sensed, for example in sensing a tensile force, the sensor may be located between the support 110 and securing member 121.

FIGS. 3C to 3F further show a movable coupling 310 that allows the sensor 130 to pivot relative to the support 110. It will be appreciated that some sensors 130, for example particular types of load cell, sense the force in a single direction, hence the movable coupling 310 allows the sensor to be aligned so that the sensing direction is substantially parallel to the exerted force. Accordingly, this will allow the sensor 130 to sense the entire force indicative of at least the hamstring strength in at least one leg, instead of a vertical component thereof.

In FIGS. 3C to 3F, the movable coupling 310 includes a ball and socket type joint, in which the ball is coupled to the support 110, and the socket is coupled to the sensor 130, thus allowing the sensor 130 rotational freedom with respect to the support 110. However, it will be appreciated that any movable coupling 310 may be used, including a swivel, tie, chain, rope, flexible cable, strap, or the like. It will also be appreciated that feature is not essential.

Figure 3G:
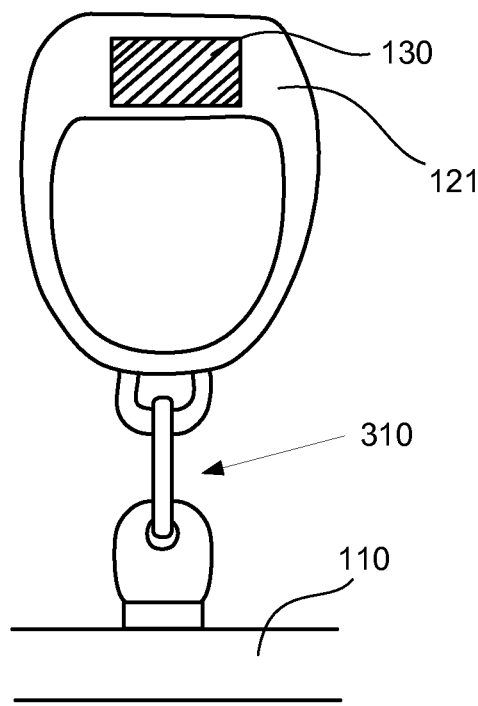
FIGS. 3G and 3H are schematic diagrams of further examples of a securing member and a sensor.
Figure 3H:
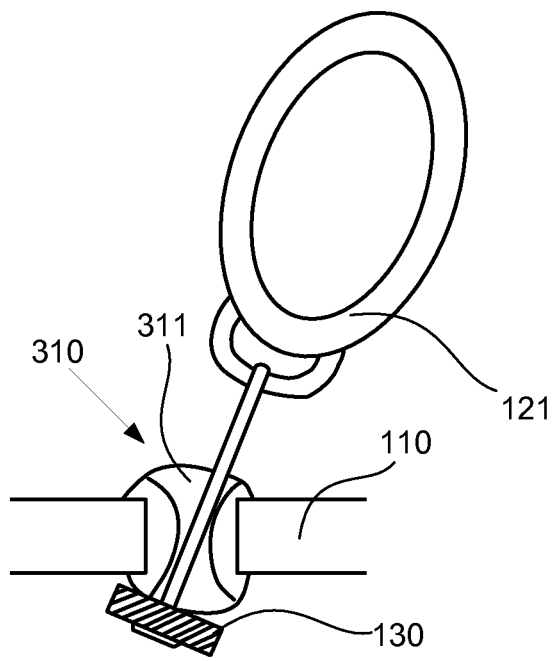

FIGS. 3G and 3H show two further examples of a securing member 121, sensor 130, and movable coupling 310. In FIG. 3G, a side of the securing member 121 is coupled to the support 110, and the sensor 130 is included in the securing member 121 in an opposing side, so that the sensor 130 senses a compressive force when the lower leg of a subject S is urged away from the support 110.

In FIG. 3H, a securing member 121 is coupled to a sensor 130 through an aperture 311 provided in the support 110. In this regard, the sensor is provided on an opposing side of the support 110 to the securing member 121, and hence is positioned to sense a compressive force when the lower leg of a subject S is urged away from the support 110. It will be appreciated that the aperture 311 may be any suitable shape, and in this example is provided to allow the movable coupling 310 to move.

Further example apparatus 100 for use in assessing hamstring strength of a subject S is shown in FIGS. 4A to 4H. Features similar to those of the example apparatus described above have been assigned correspondingly similar reference numerals.

Figure 4A:
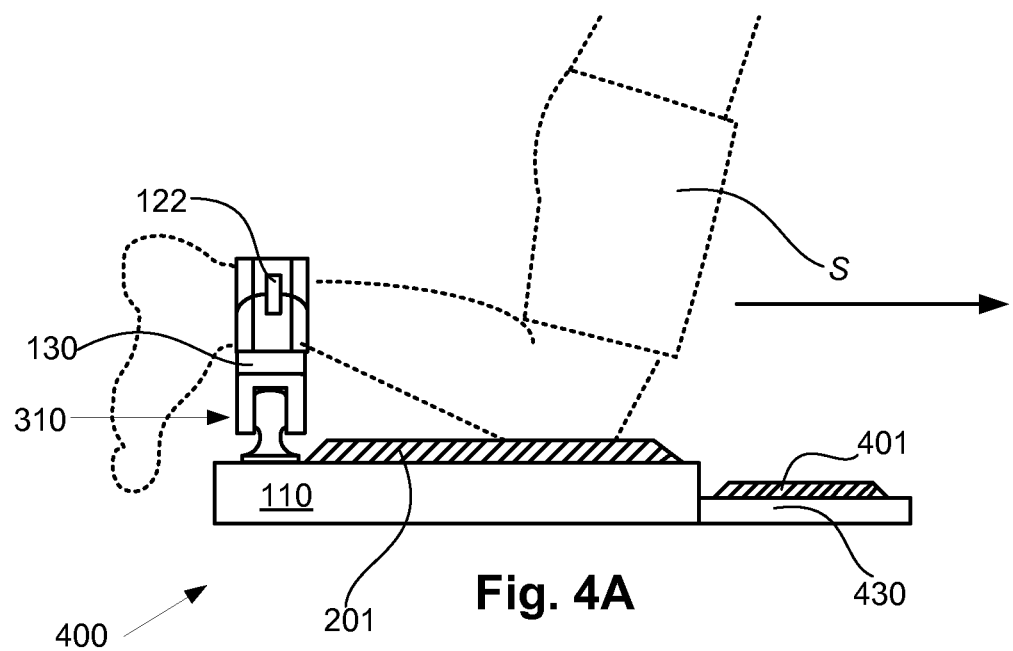
FIGS. 4A and 4B are schematic diagrams of a side and bottom-up view of a second example of an apparatus for use in assessing knee flexor strength of a subject, including an extendable portion.
Figure 4B:
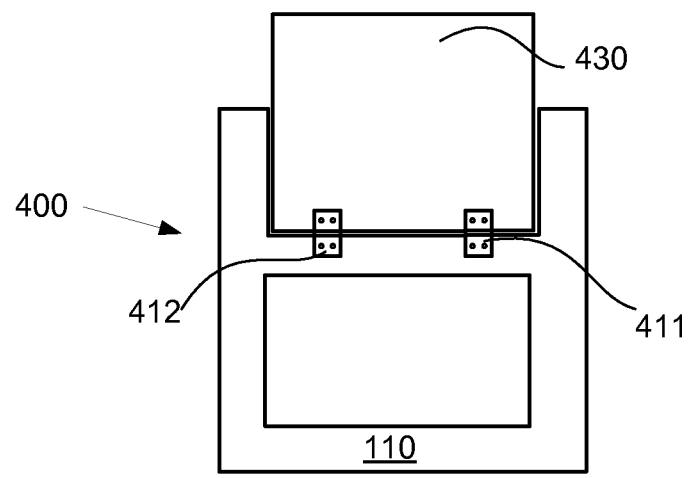

FIGS. 4A and 4B show a second apparatus 400 for use in assessing hamstring strength of a subject including a support 110, securing members 122, sensors 130 coupled to a movable coupling 310, and a knee support 201.

The apparatus further includes an extendable portion 430 including an upper body support 401 for supporting at least part of the subject's S upper body whilst the subject performs at least part of the eccentric contraction, for example as shown in FIG. 1F. In this regard, the upper body support 401 may be composed of any suitable material, for example foam, rubber, cloth, or the like. In this example, the extendable portion 430 is coupled to the support 110 using hinges 411 and 412, however it will be appreciated that any suitable form of coupling may be use, for example, the extendable portion may be provided as a separate piece that can be detachably coupled to the support 110, or in a slide-able arrangement such that the extendable portion is housed within or underneath the support 110 and slide-ably extended from there.

Accordingly, the apparatus 400 may be provided in an assembled state, with the extendable portion 430 fully extended, for example as shown in FIGS. 4A to 4E, and this allows additional comfort, stability and support for the subject while performing the eccentric contraction. Additionally, in a disassembled state, in which the extended portion is removed, slid within or underneath the support 110, hingeably folded into the support 110, or the like, the apparatus 400 becomes more manageable during transportation and storage, and hence portability is increased. Alternatively, the extendable portion 430 may be permanently provided in the assembled position, either as a separate portion to the support 110, or integrally formed with the support 110.

In this example, it will be appreciated that additionally, the one or more securing members 121, 122 may be coupled to the support 110. However, this feature is not essential.

Figure 4C:
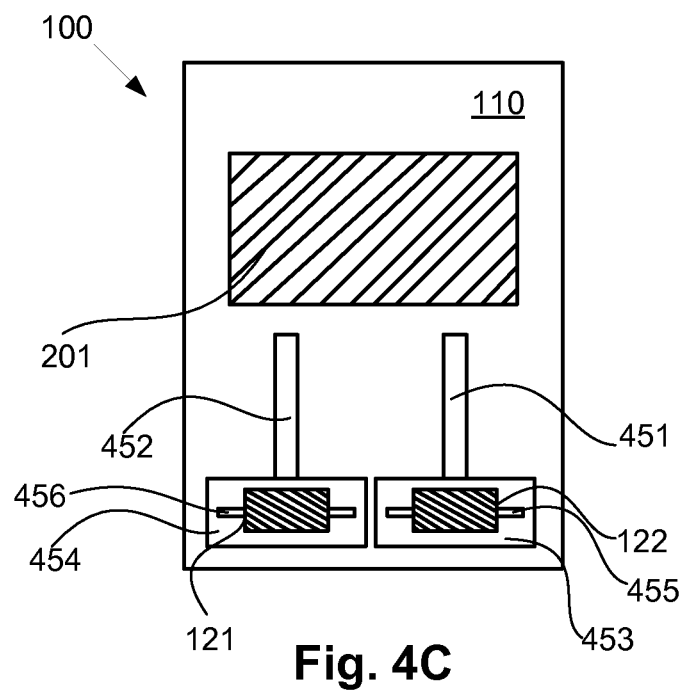
FIGS. 4C and 4D are schematic diagrams of a third example of an apparatus including securing members movably mounted to a support.
Figure 4D:
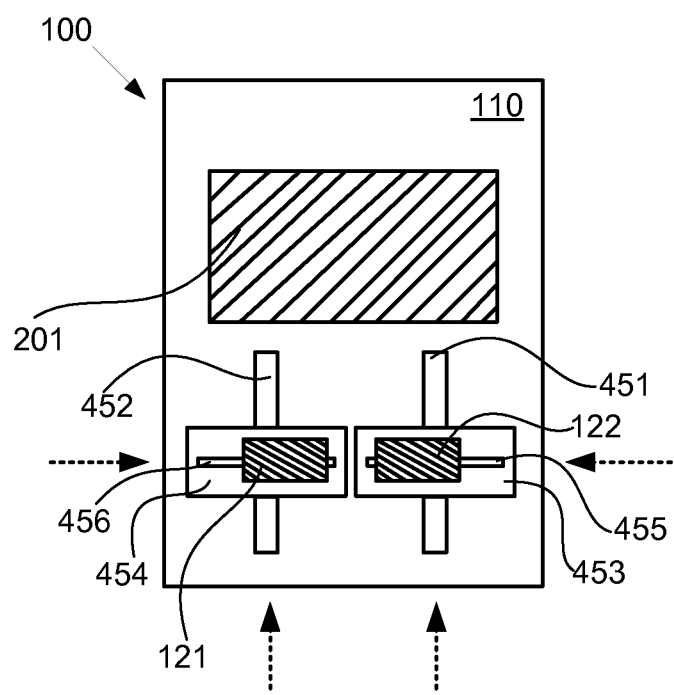
Figure 4E:
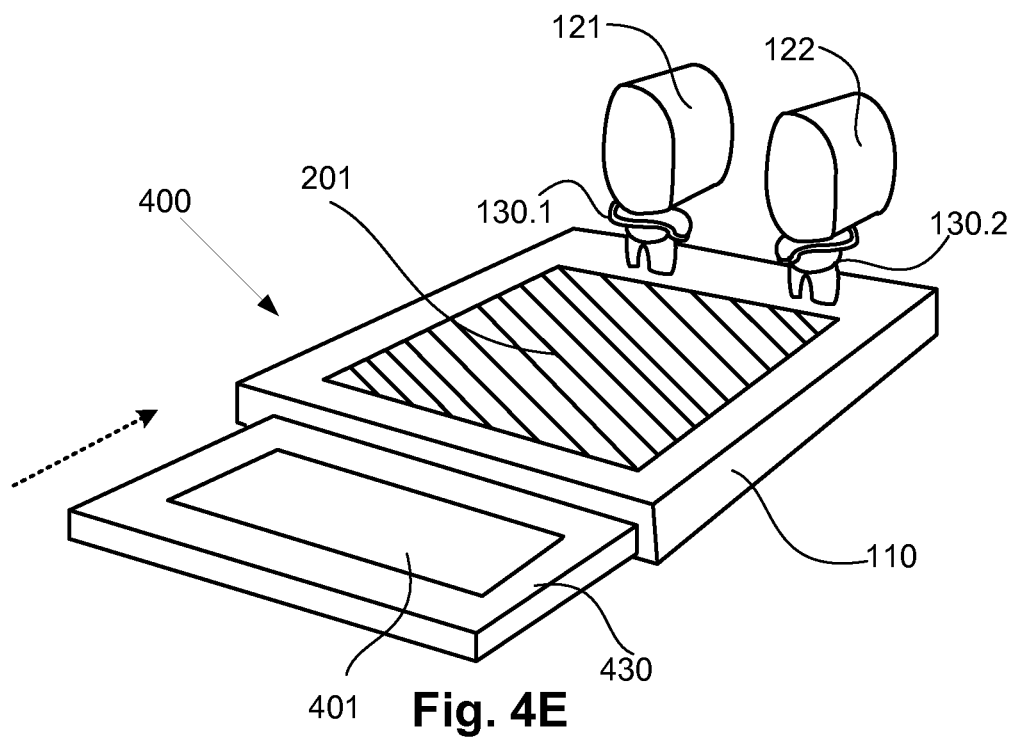
FIGS. 4E to 4G are schematic diagrams of a fourth, fifth and sixth example of an apparatus for use in assessing knee flexor strength of a subject, including an extendable portion.

FIGS. 4C and 4D include a third example of an apparatus 400 where features similar to those of the example apparatus described above have been assigned correspondingly similar reference numerals, and will not be discussed again here. It will be appreciated that the securing members 121, 122 may be movably mounted to the support 110 such that their position and/or angle relative to the support 110 may be adjusted to suit a particular muscle contraction, or a particular subject S, including different subjects with different length legs, different hip widths, or the like, or to asymmetrically arrange the securing members 121, 122 in order to asymmetrically distribute a maximal force generating capacity between the hamstrings. In this example, the securing members 121, 122 may be movably mounted such that the distance between the securing members 121, 122 may be adjusted, Additionally, the movable portions 453, 454 are movably mounted to the support 110 using second guiding members 451, 452, such that the distance between the securing members 121, 122 and the knee support 201 may be adjusted.

It will be appreciated that other movable mounting arrangements may be used, for example the first guiding members 455, 456 may used to adjust the distance between the securing members 121, 122 and the knee support 201, and the second guiding members 451, 452 to adjust the distance between securing members 121, 122. Alternatively there may be no movable portions 453, 454, such that the apparatus 400 includes only second guiding members 451, 452, in which the distance between the securing members 121, 122, or the securing members 121, 122 and the knee support 201, may be adjusted. It will further be appreciated that any suitable first and second guiding members may be used including guide rails, pins and pin holes, or the like. However this feature is not essential.

FIGS. 4E to 4H include fourth to seventh examples, respectively, of an apparatus 400 where features similar to those of the example apparatus described above have been assigned correspondingly similar reference numerals, and will not be discussed again here.

Figure 4F:
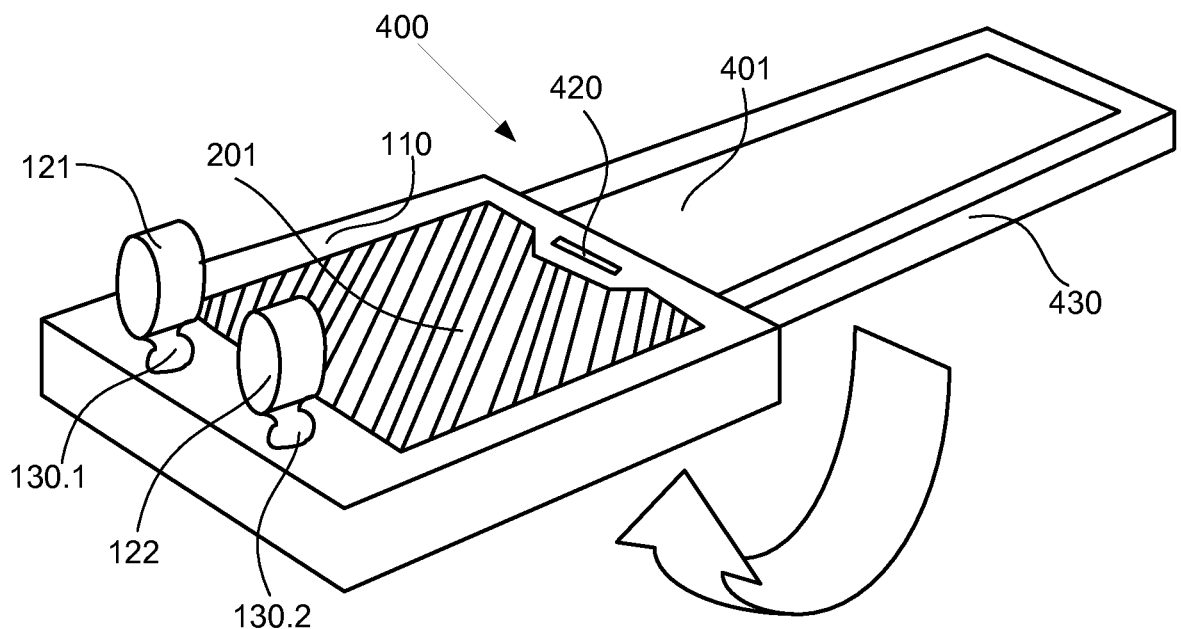
Figure 4G:
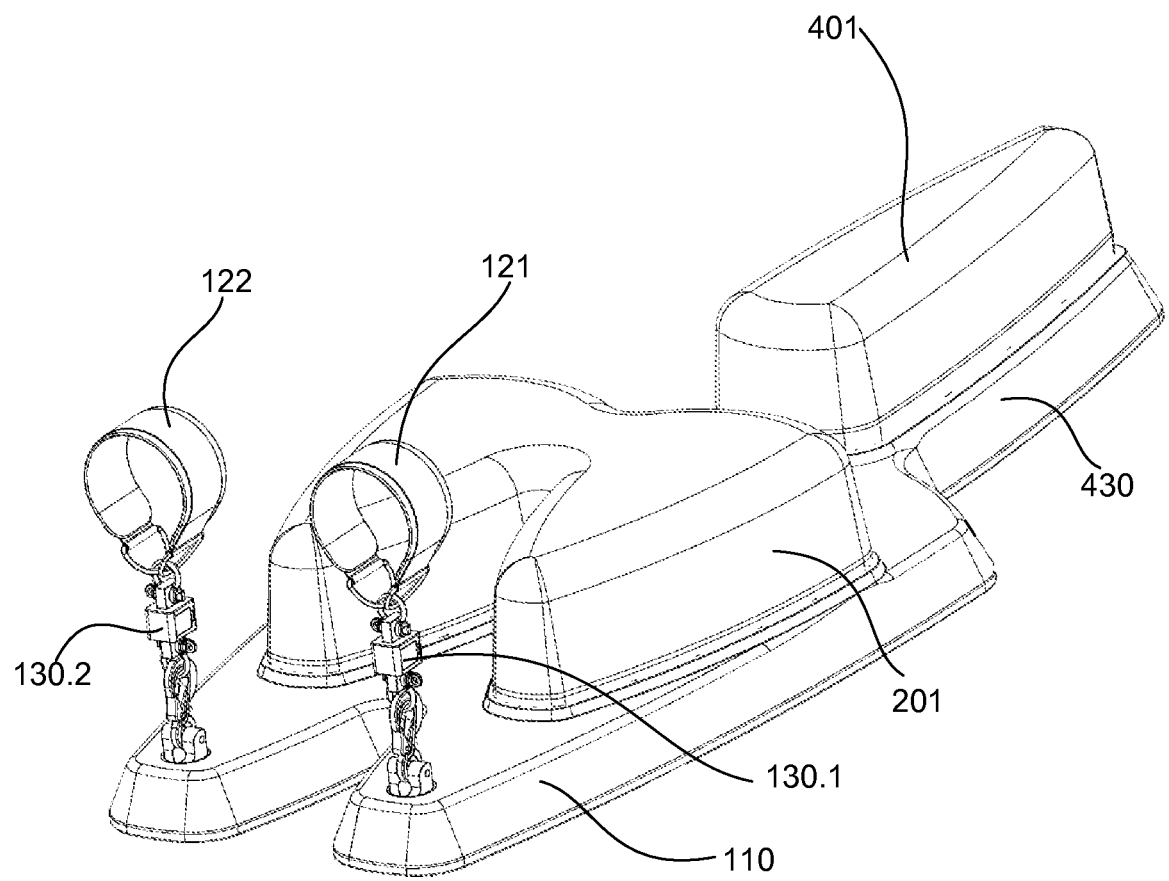
Figure 4H:
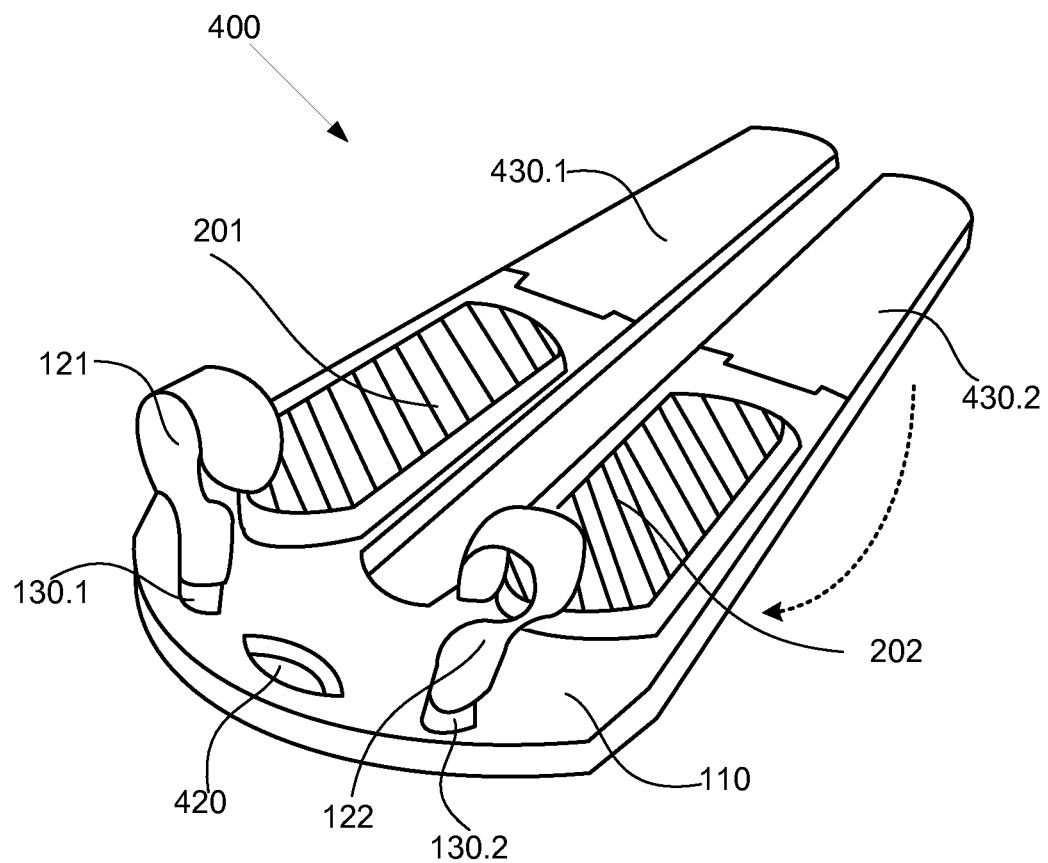
FIG. 4H is a schematic diagram of a seventh example of an apparatus for use in assessing knee flexor strength of a subject, including two extendable portions.

FIGS. 4F and 4H show apparatus 400 which further includes an aperture 420 in the support 110, such that the aperture provides, for example, a handle for ease in extending or attaching the extendable portion/s, and/or ease in transporting the apparatus 400, or the like. However this feature is not essential.

Additionally, FIG. 4H shows an apparatus 400 including two extendable portions 430.1, 430.2, and it will be appreciated that this feature may increase the portability of the apparatus 400 by decreasing weight. Additionally, two extendable portions 430.1, 430.2 allow for independent positioning and this will be described in more detail below.

Figure 5A:
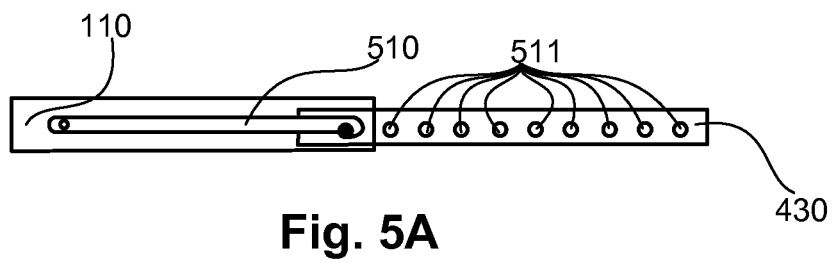
FIGS. 5A and 5B are schematic diagrams of a side view of a eighth example of an apparatus for use in assessing knee flexor strength of a subject, including an adjustable angle member.
Figure 5B:
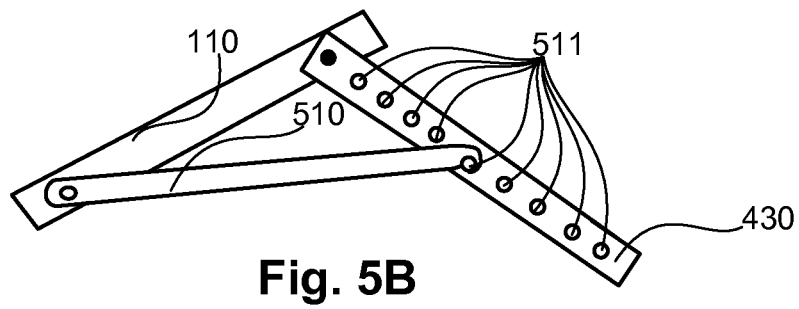
Figure 5C:
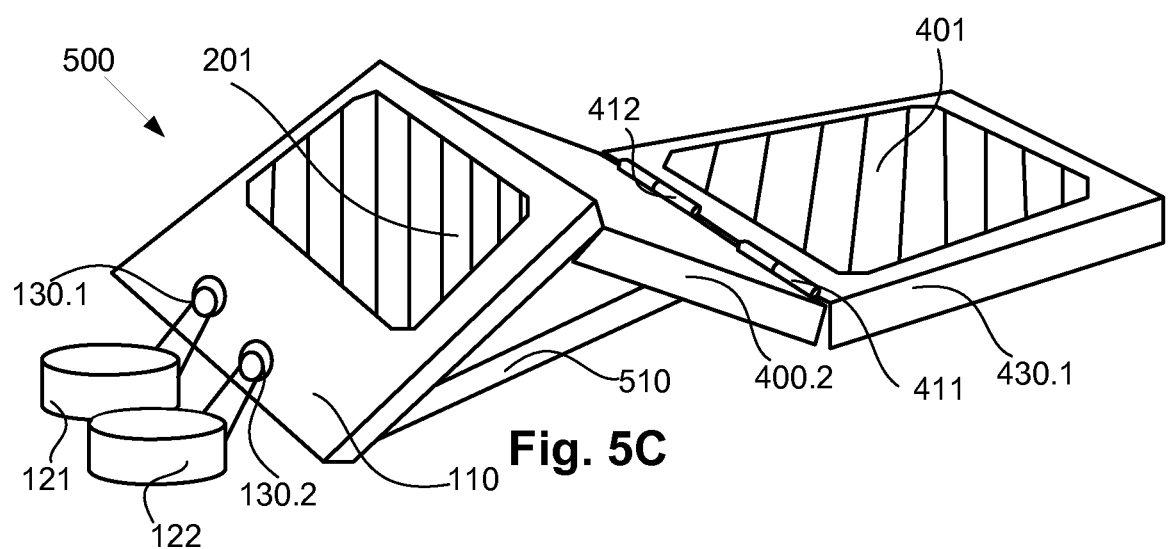
FIG. 5C is a schematic diagram of a further perspective view of the eighth example of an apparatus for use in assessing knee flexor strength of a subject, including an adjustable angle member.

A eighth example apparatus 500 for use in assessing hamstring strength of a subject S is shown in FIGS. 5A to 5C. Features similar to those of the example apparatus described above have been assigned correspondingly similar reference numerals.

FIGS. 5A and 5B show a support 110 and extendable portion 430 including an adjustable angle member 510, 511. In this respect, the adjustable angle member 510, 511 allows the support 110 and extendable portion 430 to be arranged at a desired angle, thereby allowing the initial position immediately prior to commencing an eccentric contraction of at least the hamstring, for example as shown in FIG. 1D, to be at a desired angle of incline. It will be appreciated that this angle is beneficial for performing unilateral exercise as the incline can reduce the force required to support the user during the exercise.

FIG. 5C shows an example of an apparatus 500 for use in assessing hamstring strength of a subject including a support 110, two securing members 121, 122, one or more sensors 130.1, 130.2 coupled to the securing members 121, 122 and a knee support 201 which in use supports the knee of the subject S.

In this example, the apparatus 500 includes two extendable portions 430.1, 430.2, including an upper body support 401. It will be appreciated that additional extendable portions 430.1, 430.2 can accommodate a large subject S, provide additional support to prevent unwanted movement of the apparatus 500, and/or decrease the footprint of the disassembled apparatus 500 thus increasing portability. In this respect, the support 110, and extendable portions 430.1, 430.2 are hingeably coupled via hinges 411, 412, however it will be appreciated that any suitable flexible coupling may be used.

Furthermore, the apparatus 500 in FIG. 5C includes an angle adjustment member 510, such that the support 110 and extendable portion 430 may be arranged at a desired angle, as discussed above.

A ninth example apparatus 600 for use in assessing hamstring strength of a subject S is shown in FIGS. 6A to 6C. Features similar to those of the example apparatus described above have been assigned correspondingly similar reference numerals.

Accordingly the apparatus 600 includes a support 110 and extendable portion 430, hingeably coupled via hinges 411, 412, and that different in configuration are largely aesthetic. In the example of FIG. 6C, the extendable portion 430 may be fixed at any one of a plurality of angles. In this respect, one or more angle adjustment members 621, 622 may be provided in order to secure the support 110 and the extendable portion 430 at the desired angle. It will be appreciated that a desired angle may be any suitable angle, such as the angle between support 110 and the extendable portion 430, the angle between the support 110 and the horizontal plane, the angle between the support 110 and the vertical plane, or the like.

Additionally, a plurality of markings 630 may be provided on the apparatus 600, which provide an indication of the desired angle in which at least part of the apparatus 600 may be secured. For example, anchor points on the underside of the extendable portion 430 may correspond to respective markings 630 in order to indicate the desired angle when the angle adjustment member 621, 622 is secured at that anchor point, for example using a hook, pin, or the like. However, this feature is not essential.

Figure 7A:
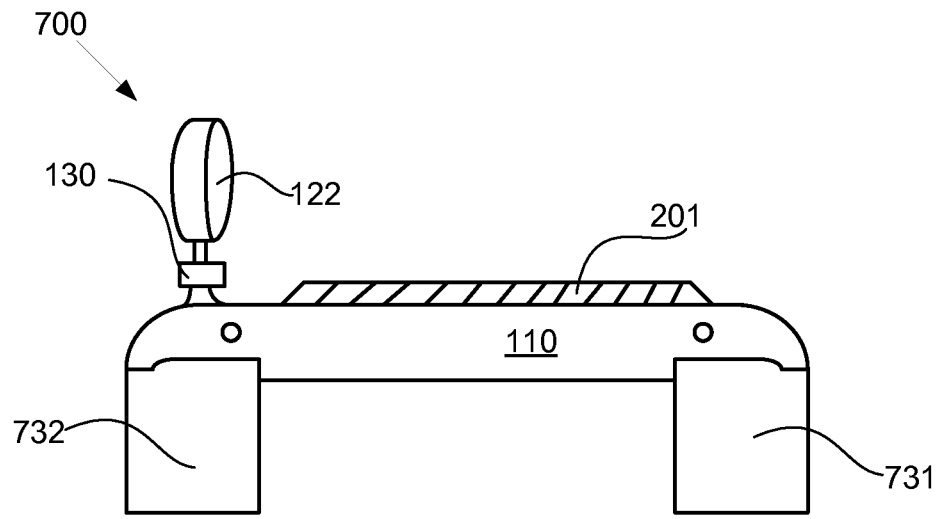
FIGS. 7A and 7B are schematic diagrams of a tenth example of an apparatus for use in assessing knee flexor strength of a subject, the apparatus including movable legs.
Figure 7B:
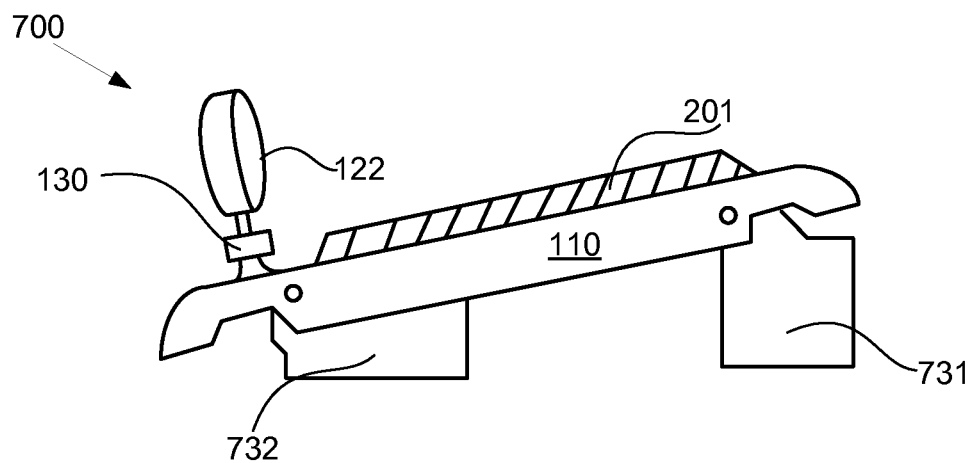

FIGS. 7A and 7B show an tenth example apparatus 700 for use in assessing hamstring strength of a subject S. Features similar to those of the example apparatus described above have been assigned correspondingly similar reference numerals.

In this example, the apparatus 700 further includes two or more movable legs 731, 732, which may be moved and/or pivoted relative to the support 110 in order to provide the support 110 at a number of different angles. In this respect, FIG. 7A of this example shows the apparatus 700 with the two or more legs 731, 732 engaged such that the support 110 is substantially horizontal, and FIG. 7B of this example shows a first leg 732 differently engaged such that the support 110 is no longer substantially horizontal. In this regard, it will be appreciated that the different arrangements of moveable legs 731, 732 may provide the support 110 at a number of different angles. However, this feature is not essential, and the apparatus 700 may be provided without movable legs 731, 732.

Figure 8A:
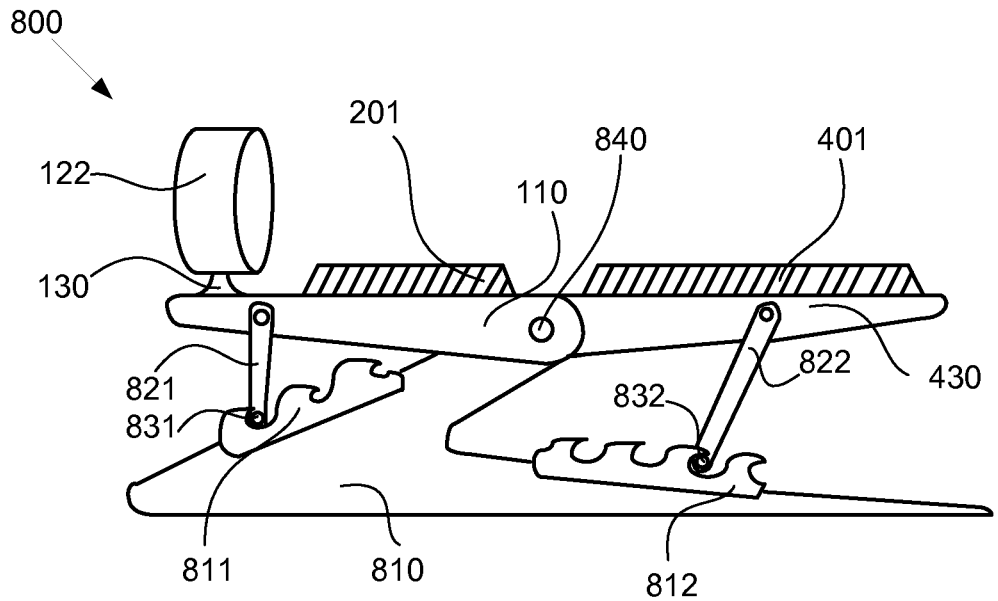
FIGS. 8A and 8B are schematic diagrams of an eleventh example of an apparatus for use in assessing knee flexor strength of a subject, the apparatus including a raised support.
Figure 8B:
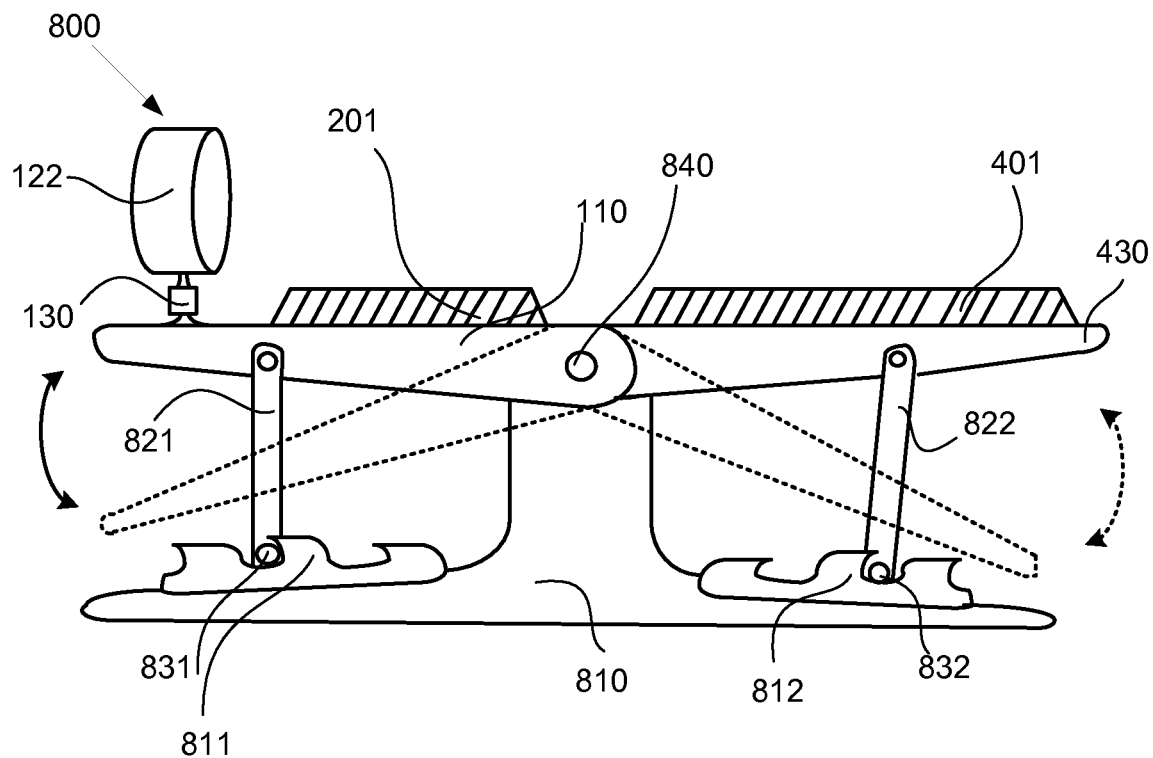

FIGS. 8A and 8B show a eleventh example apparatus 800 for use in assessing hamstring strength of a subject S. Features similar to those of the example apparatus described above have been assigned correspondingly similar reference numerals.

In this example, the apparatus 800 includes a raised support 810 and two angle adjustment members, however it will be appreciated that any number of angle adjustment members may be used. Accordingly, the angle adjustment members include a pivotally coupled elongated member 821, 822 including a catch 831, 832 that engages with any one of a plurality of teeth 811, 812, in order to secure the support 110 and/or extendable portion 430 at a desired angle. In this regard, the support 110 and extendable portion 430 may be adjusted at a desired angle around a pivot 840.

As discussed above, adjusting the position of the support 110 and/or extendable portion 430 configures the apparatus 800 for different sizes of subject S, stability of the apparatus 800, and/or different loading of the hamstrings during an eccentric contraction by the subject S.

FIG. 9A to 9G show examples twelfth to seventeen of an apparatus 900 for use in assessing hamstring strength of a subject S. Features similar to those of the example apparatus described above have been assigned correspondingly similar reference numerals.

In this example, the apparatus 900 includes one or more supports 910.1, 910.2, that are independently movable such that the supports 910.1, 910.2 may be differently positioned, thus supporting the respective lower legs of the subject in different respective positions and/or at different respective angles. Accordingly, while the subject S performs an eccentric contraction each leg will move differently and this will influence the maximal force generating capacity of each hamstring, thus the apparatus 900 may be arranged in order to induce one hamstring of the. subject S to exert a greater or lesser force than the other hamstring.

It will be appreciated this provides certain advantages including during rehabilitation it may be preferential to reduce or increase the load on a recovering hamstring. Alternatively, it may be necessary to assess hamstring strength of each leg at a range of different loads, and thus angles and/or positions. However, this feature is not essential.

Figure 9A:
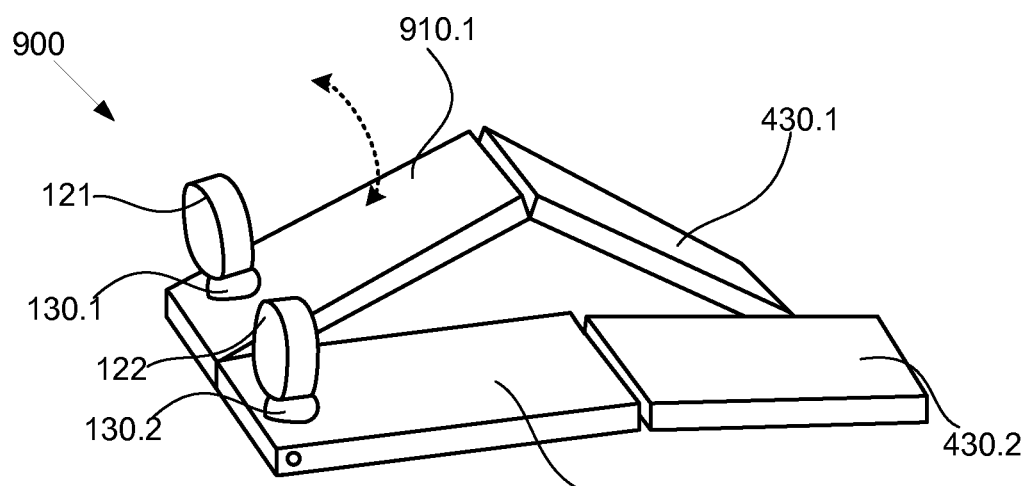
FIGS. 9A to 9G are schematic diagrams of examples twelve through seventeen of an apparatus for use in assessing knee flexor strength of a subject, the apparatus including independently adjustable supports.

In the twelfth example of FIG. 9A two extendable portions 430.1, 430.2 are hingeably coupled to the respective supports 910.1, 910.2, such they may be independently adjusted to, and secured at, a desired angle using any suitable arrangement, such as described above with reference to previous examples.

Figure 9B:
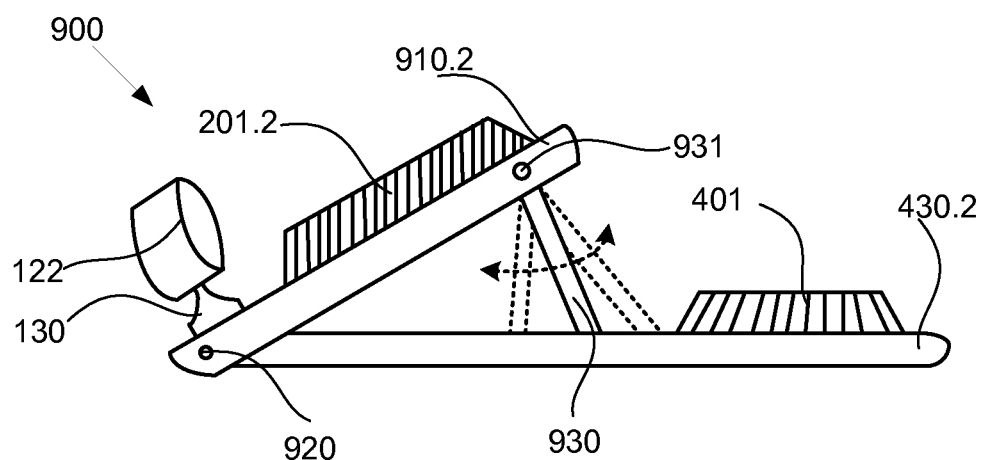

FIG. 9B shows a thirteenth example of an apparatus 900, including an adjustable angle member 930 pivotally coupled at a pivot 931 on the respective support 910.2 such that the support 910.2 move about a pivot 920 and may be secured using the adjustable angle member 930 at a desired angle.

Figure 9C:
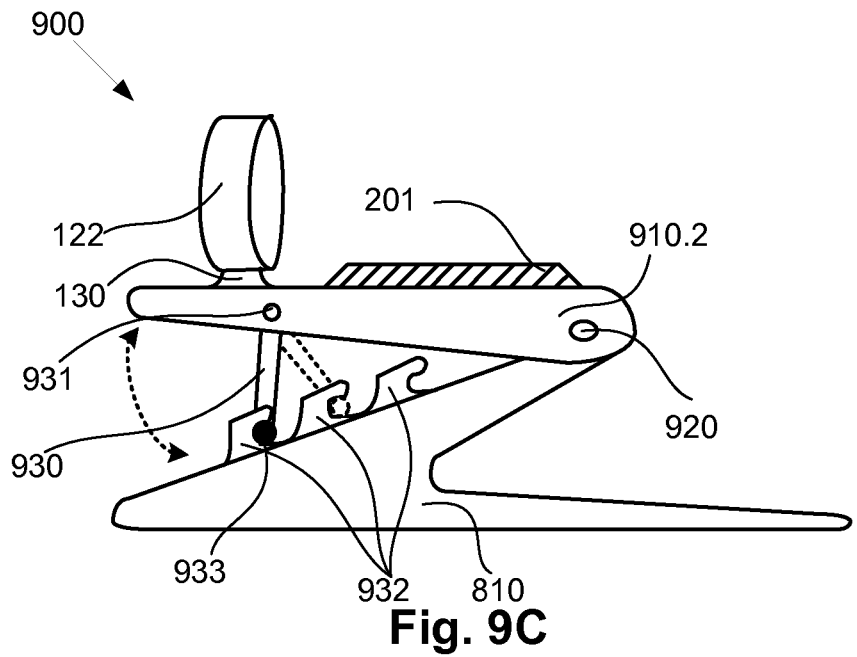

A fourteenth example of an apparatus 900 is shown in FIG. 9C, and includes an adjustable angle member 930 pivotally coupled to a pivot 931 on the respective support 910.2 such that the support 910.2 moves about a pivot 920 and may be secured using the adjustable angle member 930 at a desired angle. Accordingly, the adjustable angle member 930 includes a catch 933 that can be received in any one of a number of teeth 932 provided on a raised support 810.

Figure 9D:
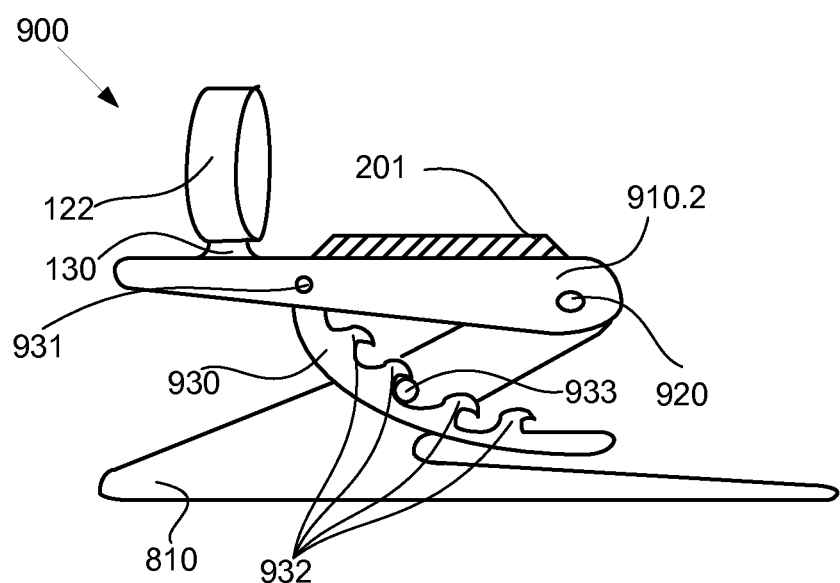

FIG. 9D includes a fifteenth example of an apparatus 900 including an adjustable angle member 930 pivotally coupled at a pivot 931 on the respective support 910.2 such that the support 910.2 moves about a pivot 920 and may be secured using the adjustable angle member 930 at a desired angle. Accordingly, the adjustable angle member 930 includes a number of teeth 932 such that any one of the teeth 932 can be received by a catch 933 provided on a raised support 810.

Figure 9E:
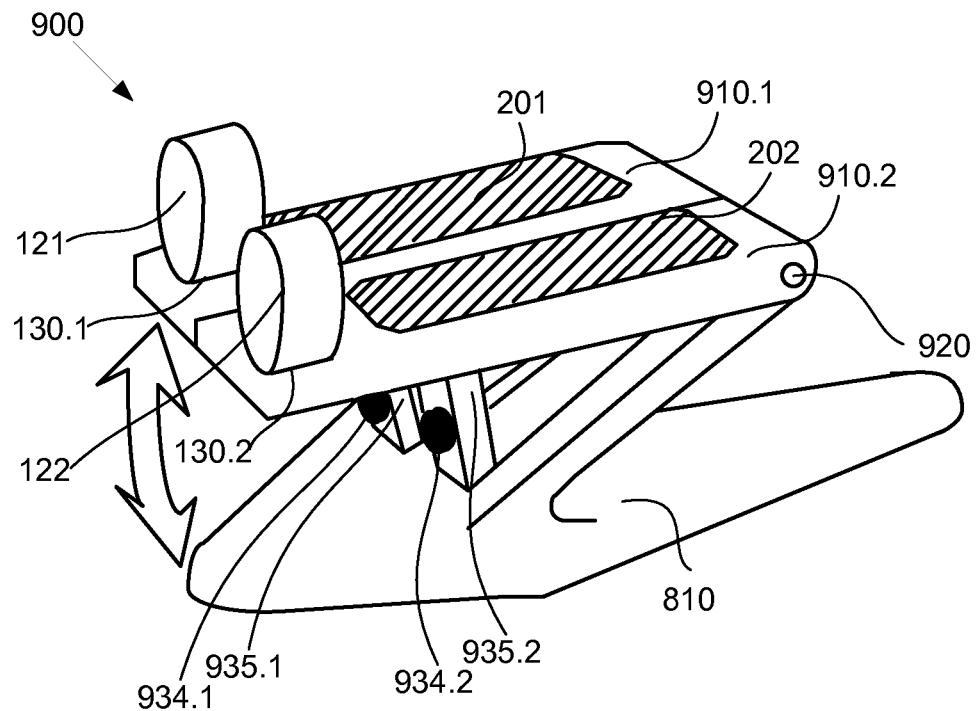
Figure 9F:
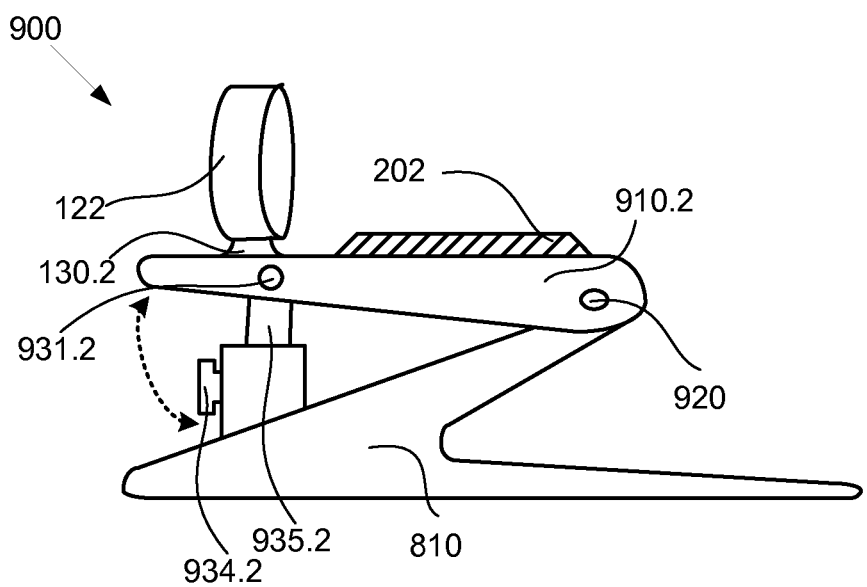

In a sixteenth example, shown in FIGS. 9E and 9F, the apparatus 900 includes adjustable angle members 935.1, 935.2 pivotally coupled to a pivot 931.2 on the respective support 910.1, 910.2 such that the supports 910.2 move about a pivot 920 and may be secured using the adjustable angle member 935.1, 935.2 at a desired angle. Accordingly, the adjustable angle members 935.1, 935.2 may be used to secure the respective supports 910.1, 910.2 at the desired angle using a respective pin 934.1, 934.2 that engages the adjustable angle member and raised support 810.

Figure 9G:
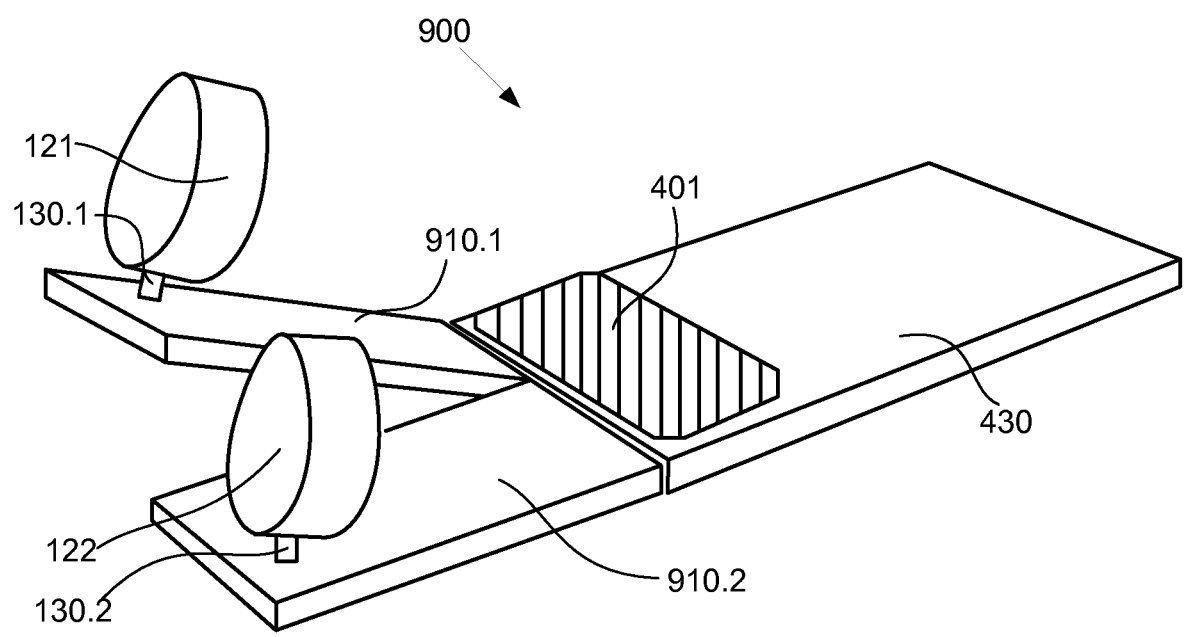

FIG. 9G shows a seventeenth example of an apparatus 900, including a single extendable portion 430, and two supports 910.1, 910.2 in which the position and/or angle of the supports 910.1, 910.2 may be adjusted independently. In this respect, the supports 910.1, 910.2 are hingeably coupled to the extendable portion 430, and they may be secured using any suitable arrangement, such as described above with reference to previous examples.

Figure 10A:
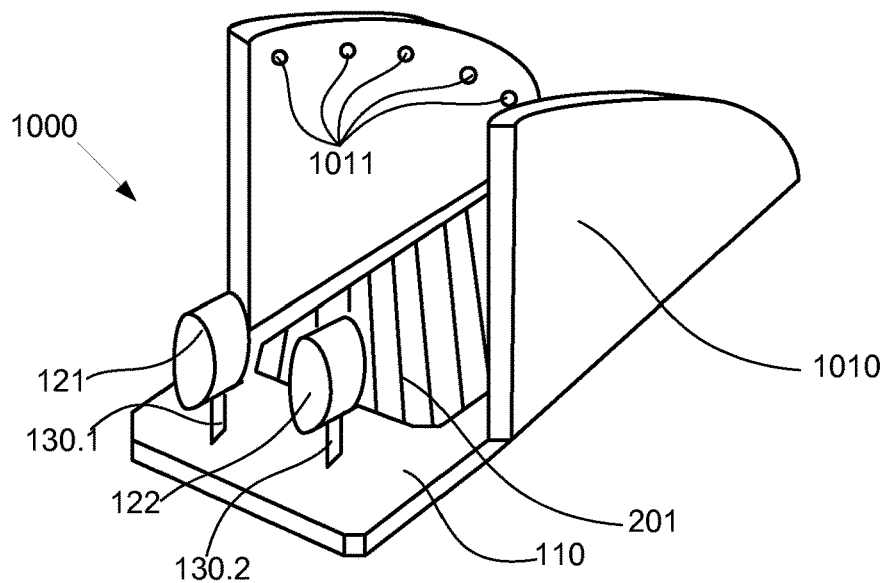
FIGS. 10A, 10B, and 10C are schematic diagrams of examples eighteen through twenty of an apparatus for use in assessing knee flexor strength of a subject, the apparatus including an angle sensor.
Figure 10B:
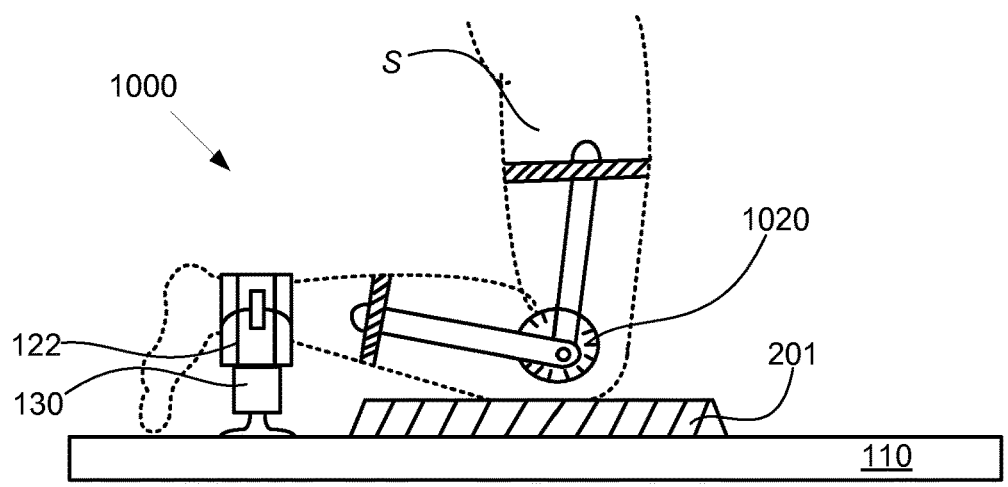
Figure 10C:
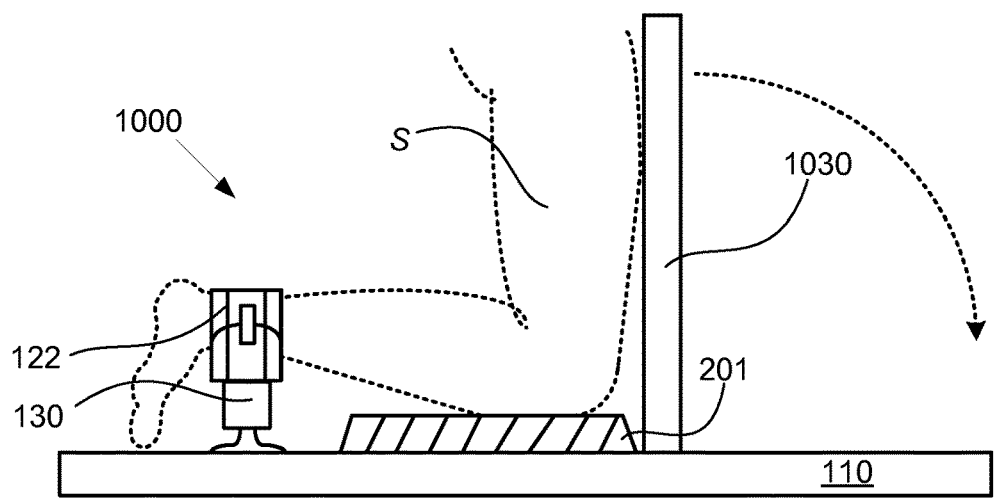

Further examples of an apparatus 1000 for use in assessing hamstring strength of a subject S are shown in FIGS. 10A to 10C. Features similar to those of the example apparatus described above have been assigned correspondingly similar reference numerals.

The apparatus 1000 includes a support 110, two securing members 121, 122 for securing a respective lower leg of the subject S, one or more sensors 130.1, 130.2, and one or more knee supports 201 which in use support the knee of the subject S.

The apparatus 1000 further includes an angle sensor for sensing the angle of the subject's knee. This information can be analysed to provide the position, angle, angular velocity, angular acceleration, or similar, of the subject while performing an eccentric contraction of at least the hamstring. It will be appreciated that the angle sensor includes any suitable arrangement, mechanism or device. For example, in FIG. 10A, the angle sensor includes two side supports 1010, in which one side support includes a plurality of emitters 1011, such as light emitting diodes (LEDs), infrared (IR) emitters, or the like. The opposing side support includes one or more angle sensors, including photodiodes, IR sensors, or the like. It will be appreciated that as a subject S performs an eccentric contraction similar to FIGS. 1D to 1F, the subject's torso will sequentially obscure each emitter from a respective angle sensor, thus allowing an indication of the angle of the subject's torso to be determined.

In FIG. 10B, the angle sensor arrangement includes any suitable mechanism for determining the angle of the subject's knee joint, including at least one goniometer 1020, gyroscope, accelerometer, magnetometer, infrared sensor or the like.

FIG. 10C shows a further example of an angle sensor, including one or more movable members 1030 which in use track the position of the user's upper leg. Accordingly, an appropriately positioned sensor or transducer, such as on a hinge located between the movable members 1030 and support 110 can sense the signal indicative of at least the angle or angular velocity of the movable member 1030.

Additionally or alternatively, in this example the movable members 1030 may provide assistance to the subject S in returning from a prone position, for example as shown in FIG. 1F, to a kneeling position, for example as shown in FIG. 1D. In this regard, the moveable member 1030 may be utilised to assist the subject S in performing a concentric contraction of at least the hamstring, as discussed above, or simply to assist the subject S in recovering the initial position following an eccentric contraction of at least the hamstring, also as discussed above. In this regard, the movable members 1030 may include any suitable arrangement for returning to an upright position, including a biasing member, a mechanical and/or electrical actuator, or the like.

It will be appreciated that the angle sensor may be used to determine an indication of the angle and/or position of the knee joint of the subject S including any one of an absolute or relative angle, angular velocity, angular acceleration, or the like, either instantaneously at temporal units throughout the exercise or averaged using an appropriate average. It will be appreciated that the indication of the angle may be subsequently used to provide further indicators or assessments, and this will be discussed in more detail below.

Furthermore, a distance such as the distance between the subject's knee axis of rotation and the sensor 130.1, 130.2 and/or securing member 121, 122 may be sensed by the angle sensor, or any other suitable arrangement, and may be used in generating the indicators or assessments, for example torque, as discussed below. Alternatively the distance may be measured manually and input into an electronic processing device, and this will also be discussed in more detail below. However, this feature is not essential.

Optionally, sensors 130.1, 130.2 may be coupled to a monitoring device or other electronic processing device, such as a processing system, which is adapted to monitor signals from the one or more sensors 130.1, 130.2 and, generate at least in part using the signals an indicator that is indicative of the hamstring strength for one or more hamstrings.

The processing system 1100 is adapted to receive signals from the one or more sensors 130.1, 130.2, and then either to display a relevant indicator, such as an indication of a measured force, or alternatively transfer signals or data derived therefrom to a separate remote device for additional processing, analysis or display. Thus, it will be appreciated that the electronic processing device can either act as an acquisition unit, or to both acquire and at least partially analyse or display results.

Figure 11:
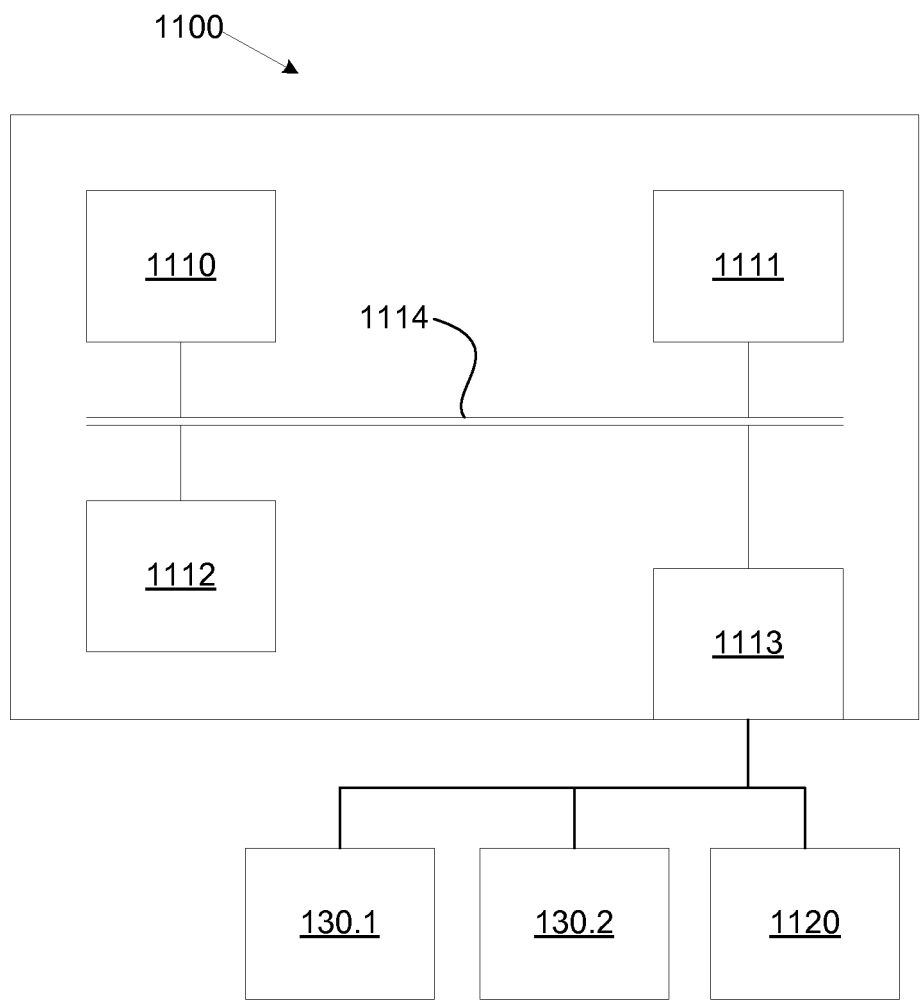
FIG. 11 is a schematic diagram of an example of an electronic processing device; and, FIG. 12 is a flow chart of a second example of a method for assessing knee flexor strength of a subject; and, FIGS. 13A to 13C are graphs of force, angle and angle velocity measured for a subject undergoing a knee flexor eccentric contraction.

Accordingly, the processing system 1100 can include any suitable form of electronic processing system or device that is capable of receiving and either interpreting or transmitting signals from the one or more sensors 130.1, 130.2. An example of a processing system is shown in FIG. 11.

In this example, the processing system 1100 includes a processor 1110, a memory 1111, an input/output (I/O) device 1112, such as a keyboard and display, and an external interface 1113 coupled together via a bus 1114. It will be appreciated that the I/O device may further include an input, such as a keyboard, keypad, touch screen, button, switch, or the like which thereby allowing a user to input data. The external interface 11.13 is used for coupling the processing system 1100 to peripheral devices, such as an output 1120 and the one or more sensors 130.1, 130.2, as well as to devices, such as communications networks, databases, other storage devices, or the like. Although a single external interface is shown, this is for the purpose of example only, and in practice multiple interfaces using various methods (e.g. Ethernet, serial, USB, wireless (such as Bluetooth®, Zigbee®, radio frequency networks), mobile networks or the like) may be provided. It will also be appreciated that additional hardware components, may be incorporated into the processing system 1100, depending on the particular implementation.

It will further be appreciated that the electronic processing device 1100 may include any suitable power supply (not shown), for example, a battery, a solar panel, or the like, however this is not essential, and alternatively, the electronic processing device 1100 may be adapted to connect to mains power, an electricity grid, or the like.

In use, the processor 1110 executes instructions in the form of applications software stored in the memory 1111 to allow signals from the one or more sensors 130.1, 130.2 to be interpreted and optionally used, for example to control the output 1120. Accordingly, for the purposes of the following description, it will be appreciated that actions performed by the processing system 1100 are typically performed by the processor 1110 under control of instructions stored in the memory 1111, and this will not therefore be described in further detail below.

Accordingly, it will be appreciated that the processing system 1110 may be formed from any suitably programmed processing system, such as a suitably programmed PC, Internet terminal, lap-top, hand-held PC, tablet PC, slate PC, iPad™, mobile phone, smart phone, PDA (Personal Data Assistant), or other communications device. Accordingly, the processor 1110 can be any form of electronic processing device such as a microprocessor, microchip processor, logic gate configuration, firmware optionally associated with implementing logic such as an FPGA (Field Programmable Gate Array), or any other electronic device, system or arrangement capable of interacting with the one or more sensors 130.1, 130.2 and optionally the output 1120.

It will be appreciated that the apparatus 100 may further include an output 1120 for, presenting the indicator to the user. In this regard, the output 1120 may include any suitable mechanism, including a light emitting diode (LED), sound emitting member such as a speaker or the like, a digital display such as a monitor or the like, an electronic signal emitting member such as a USB or Ethernet port, wireless transmitter, or similar. Accordingly, it will be appreciated that the output 1120 may generate one or more of a light, including a coloured light, a sound or tone, at least one alphanumeric character, a graph, a picture, a wireless electronic signal, a wired electronic signal, or the like.

An example of a method of assessing hamstring strength of a subject S will now be described. The method includes using an apparatus 100 that includes a support 110, two securing members 121, 122, and one or more sensors 130.1, 130.2.

The method includes securing two lower legs of a subject S using the respective securing members 121, 122, at a position that is in use substantially fixed relative to the support 110. The method further includes sensing a force indicative of at least the hamstring strength in one or two legs of the subject S using the sensor 130.1, 130.2 while the subject S performs an eccentric contraction of at least a hamstring.

Figure 12:
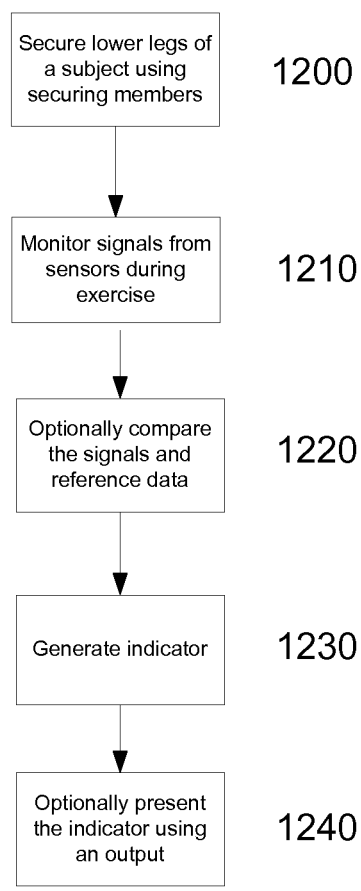

A further example of a method of assessing hamstring strength of a subject S will now be described with reference to FIG. 12. The method includes using an apparatus 100 that includes a support 110, two securing members 121, 122, and one or more sensors 130.1, 130.2.

Prior to step 1210, the securing members 121, 122 and one or more optional knee supports 201, may be adjusted and secured in a position suitable for the size and shape of the subject S. For example, the distance between the securing members 121, 122 may require adjusting, or the distance between the securing members 121, 122 and the knee support 201. Furthermore, the support 110 and/or extendable portion 430 may be positioned at a desired angle in order to different assess one or both hamstrings of the subject S, according to any one of the arrangements described above with reference to previous examples. However, these steps are not essential.

At step 1200, the two lower legs of the subject S are secured using the respective securing members 121, 122, at a position that is in use substantially fixed relative to the support 110. Accordingly, it will be appreciated that additional securing members 121, 122 may be provided on the apparatus 100 to secure further parts of the lower legs to the apparatus 100, for example providing four securing members 121, 122 to secure respective ankles and knees of a subject S, however this feature is not essential and only two securing members 121, 122 may be used.

At step 1210, the signals from one or more sensors 130.1, 130.2 are monitoring while the subject S performs at least one eccentric contraction of at least a hamstring. Typically, the signals are monitored using an electronic processing device, such as a processing system, which is adapted to receive and interpret the signals. In one example, two sensors 130.1, 130.2 are coupled to respective securing members 121, 122 such that the sensors 130.1, 130.2 sense the force indicative of a least the hamstring strength in each leg of the subject S, for example simultaneously or at different times. Furthermore, the eccentric contraction of at least a hamstring includes any suitable exercise, for example the 'Nordic hamstring exercise' described above with reference to FIGS. 1D to 1F.

Optionally, at step 1220 the signals, at least in part, are compared to reference data, which includes any suitable data as discussed above with reference to FIG. 11.

At step 1230, an indicator indicative of the hamstring strength is generated from the signals, at least in part, and include any suitable indicator, for example as described above with reference to FIG. 11. In the event that optional step 1220 is performed, the indicator may be generated in accordance with the results of the comparison.

Furthermore, the indicator may be generated from an average based on, at least in part, the signals acquired during the eccentric contraction. For example, at step 1210, the signals from the sensors 130.1, 130.2 may be monitored while the subject performs a plurality of eccentric contractions, thus allowing the indicator at step 1230 to be generated using an average of at least some of the signak Optionally, outlying signals may additionally be discarded, for example, if a subject performs a set of six eccentric contractions at step 1210, the indicator generated at step 1230 may include an average determined using, at least in part, the signals corresponding to the four eccentric contractions performed in the middle of the set.

Optionally, at step 1240, the indicator is presented to the user on an output 1120, for example as discussed above with reference to FIG. 11.

It will be appreciated that the indicator may be indicative of one or more of an instantaneous force, an average force, a peak force, an instantaneous torque, an average torque, a peak torque, an impulse, work, rate of force and/or torque development, or the like. Furthermore, the indicator may be bilateral, and thus indicative of at least the hamstring strength in both legs, or unilateral, and thus indicative of at least the hamstring strength in one or each leg of the subject S. Additionally, the indicator may include an average such as an aggregate average, a weighted average, a moving average, for example weekly or monthly averages, or any other suitable average.

However, additional indicators can be generated that are indicative of other parameters, such as the knee joint position, movement, or the like, as described below.

Figure 13A:
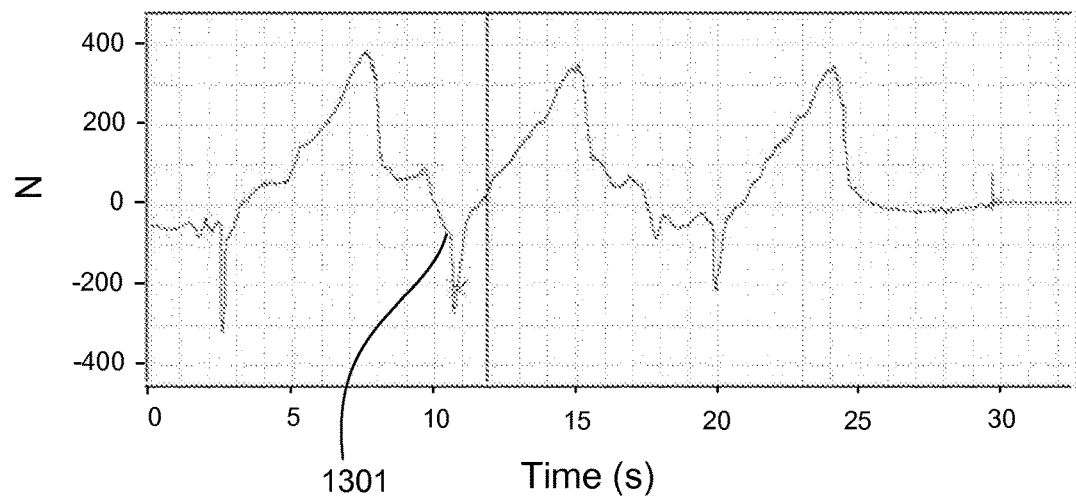

Temporal units, for example with respect to instantaneous indicators, may also be included. In this respect, FIG. 13A provides an example of an indicator 1301 including a force indicative of at least the hamstring strength, per temporal unit, in a leg of a subject S while the subject S performs an eccentric contraction of at least the hamstring.

Figure 13B:
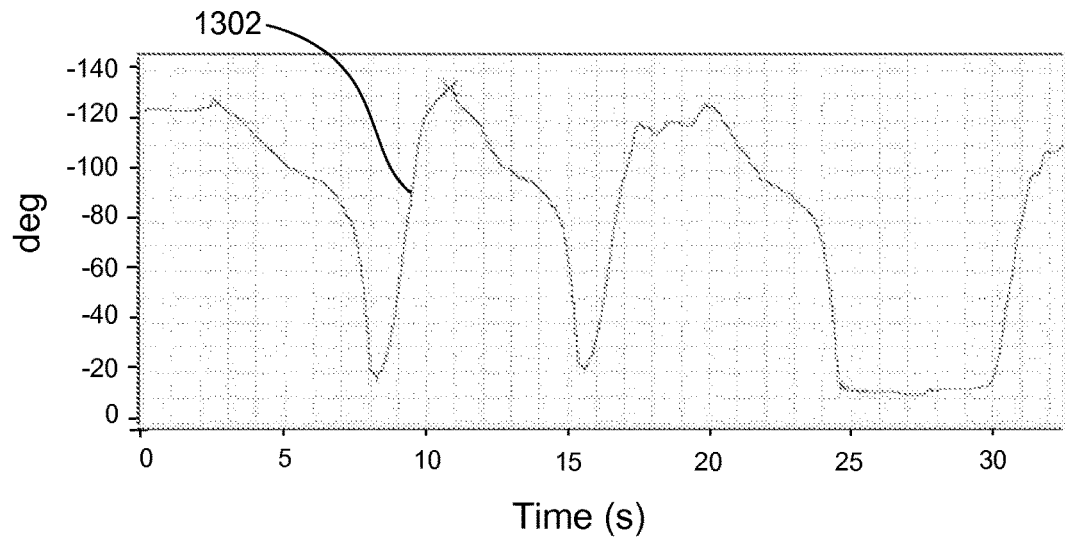
Figure 13C:
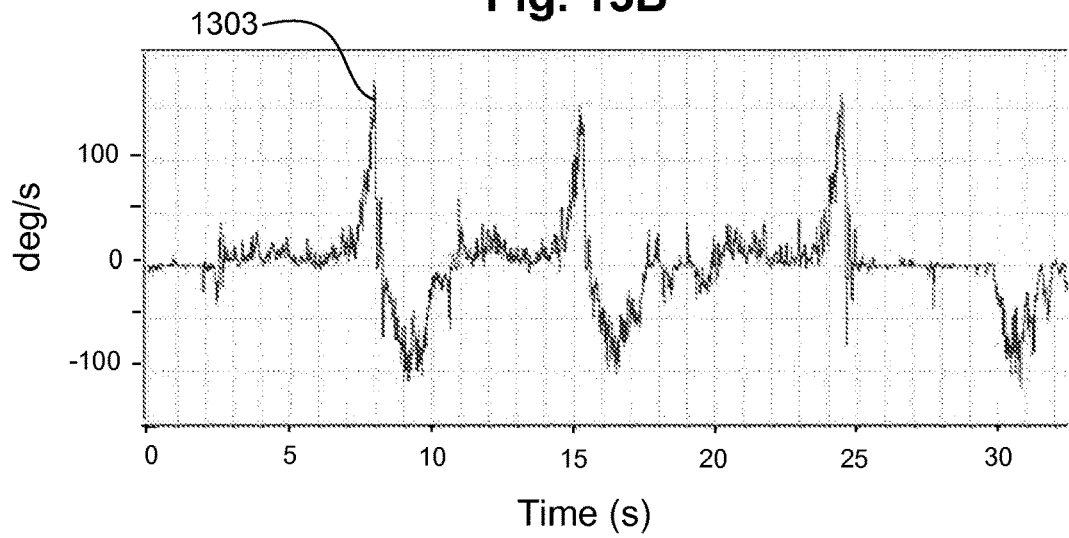

FIGS. 13B and 13C provide examples of knee joint position 1202 and knee angular velocity 1203, respectively, with respect to time, which may be provided in addition to, or used in determining, an indicator. In this regard, it will be appreciated that the knee joint position 1202 and knee angular velocity 1203 may be measured using any suitable arrangement, for example the arrangements discussed with respect to FIGS. 10A to 10C.

Additionally or alternatively, the processing system may compare the signals from at least one of the one or more sensors 130.1, 130.2, and reference data, and generate the indicator in accordance with the results of the comparison. In this regard, the reference data may include any suitable data, for example a tolerance determined from a normal population, a predetermined range, a predetermined reference, a previously generated indicator, and an indicator generated for another leg.

Furthermore, the indicator may be indicative of both the signals, and optionally reference data. The indicator can include a graphical depiction of the signals next to or overlaid over a population reference, or previously generated indicator from the same subject S and/or leg. Alternatively or additionally, the indicator includes a difference between the signals, at least in part, and the reference data, for example a quantitative improvement in hamstring strength from a previously generated indicator, or a percentage difference in hamstring strength between legs of a subject S. Further, the indicator may include a ratio between the signals, at least in part, and the reference data, for example a ratio between the hamstring strength of respective legs of a subject S, or a ratio between hamstring strength and other muscle/muscle group strength, such quadricep(s) strength or hip flexor(s) strength, of a subject S.

Accordingly, it will be appreciated that the indicator may provide an indication of hamstring strength imbalance between respective legs of a subject S, hamstring fatigue or fatigability, improvement in hamstring strength, for example during rehabilitation, or a benchmark indication, for example with respect to a general population, or population of elite athletes, population of sportspeople in a similar sport, or the like. In this regard, the indicator may be indicative of longitudinal analysis of a subject S, however this feature is not essential and indicators may be sent to, and stored on a separate electronic processing device capable of performing longitudinal analysis.

A number of experiments were performed in order to demonstrate the effectiveness of the abovementioned apparatus 100, and these are discussed in more details below. In this regard, an arrangement similar to FIGS. 1A to 1C was used.

Reliability and Validity Experiments

Thirty-one recreationally active males (22.46±2.33 years; 1.81±0.06m; 80.52±8.48 kg) participated in the study, with most competing in Australian football, rugby (league, union or touch), soccer or sprinting. One participant was excluded from the study for continually changing their technique of the Nordic Hamstring Exercise (NHE), between sessions, resulting in a total of thirty participants for analysis. Of these thirty participants, one individual had continual difficulty in performing contractions on the isokinetic dynamometer and was excluded from correlation analysis. All participants were free of any injury to the lower limbs and were fully active in their chosen sport at the time of testing. All testing procedures were approved by the University Human Research Ethics Committee. Participants gave informed written consent prior to testing after having all procedures explained to them.

All participants reported to the laboratory on three separate occasions. The first session acted as a familiarisation session to prepare participants for all procedures to be performed in subsequent sessions and to correct any technique faults during the performance of the NHE. The second session involved the determination of eccentric knee flexor strength via isokinetic dynamometry (torque) and the apparatus 100 (force). The final session involved the assessment of eccentric knee flexor force via the apparatus 100 only, to allow for test-retest reliability to be determined.

Following a warm up set of submaximal bilateral NHEs, participants were asked to perform two sets of three maximal NHEs bilaterally (with both legs) and unilaterally (using only one leg) resulting in a total of four sets and 12 contractions per leg. With respect to testing order of the different conditions, bilateral contractions were always performed before unilateral contractions, with the order of limbs tested unilaterally randomised between participants. The between set rest period was set at two minutes Participants were instructed to gradually lean forward at the slowest speed possible with the trunk held in a neutral position throughout (similar to FIGS. 1D, 1E, and 1F) whilst the investigators gave verbal encouragement throughout the range of motion to ensure maximal effort. At the completion of the lowering phase the participants slowly returned themselves to the starting position to preparation for the following set. Technique for all repetitions was monitored visually by the investigators and individual repetitions were rejected if they were not performed with correct technique.

Assessment of eccentric knee flexor strength was also performed on a Biodex Systems 3 Dynamometer (Biodex Medical Systems, Shirley, NY). Participants lay prone with the hips in a neutral position with the lateral epicondyle of the femur carefully aligned with fulcrum of the dynamometer. This position was selected to mimic the muscle lengths experienced by the hamstring muscles during the NHE. The tested leg was attached to the lever of the dynamometer via a Velcro™ strap and padded restraints were fastened across the hips to isolate movement to the knee joint. The range of motion was set at 5°-90° of knee flexion (0°=full knee extension) and correction for limb weight was performed. Three sets of four submaximal contractions of the knee flexors were performed at $+240°.s^{-1}$ as a warm-up to prepare the participant for maximal effort in the following sets. Eccentric torque assessment consisted of two sets of three consecutive maximum voluntary contractions (MVC) of the knee flexors at speeds of $30°.s^{-1}$ and $120°.s^{-1}$ with 60 seconds rest between sets. These speeds were selected as pilot testing identified these angular velocities encompassed the range of the knee joint angular velocities during the terminal phase of the NHE. Athletes were given verbal encouragement from the investigators to ensure maximal effort throughout the range of motion. At the completion of each contraction the investigators returned the lever to the starting position in preparation for the next repetition. The leg and speed testing orders were randomised.

Force data for both limbs during the NHE, and torque and lever position data during isokinetic dynamometry, was transferred to a computer at 1 kHz through a 16-bit Power-Lab 26T AD recording unit (ADInstruments, New South Wales, Australia) and stored for later analysis. On the apparatus 100, for both limbs (left/right) and conditions (bilateral/unilateral), the highest force for each contraction was determined and maximal force generating capacity was expressed as an average of the peak from six contractions (average peak force) and as the single highest peak of six contractions (peak force). Dynamometer maximal torque was determined as per the experiment device at the two isokinetic speeds ($30°.s^{-1}/120°.s^{-1}$) however only average peak torque was reported as we have found that this is a more reliable method than a single peak torque measure. The ratio of between limb force or torque is presented as left leg: right leg for both devices.

All statistical analyses were performed using JMP® version 10.0 (SAS Institute®, Inc). Means and corresponding standard deviation for all force variables from the apparatus 100 were reported for left and right limbs and for between limb force ratios. A spreadsheet by Hopkins 'A new view of statistics' (2000) *Internet Society for Sports Science* www.sportsci.org/resource/stats.html (accessed November 2010), was used to calculate interclass correlation (ICC), typical error (TE) and TE % as a co-efficient of variation (CV). Effect size was determined from test 1 and test 2 comparisons to evaluate the magnitude of the difference. For reliability an ES (mean difference/pooled SD) of <0.2 was expected. The smallest worthwhile change (SWC) (0.2× ((Stdev Test 1+Stdev Test 2)/2) was also determined. Bivariate correlation analysis was used to assess concurrent validity between reciprocal measures of strength from the apparatus 100 (dependent variable) and gold standard isokinetic dynamometer (independent variable).

Descriptive statistics for all force variables, generated from the apparatus 100, for both test 1 and 2 are presented in Table 1. In addition, the magnitude of the differences from test 1 to test 2 is reported as effect size. One variable, bilateral peak force on the right leg, displayed a detectable difference (effect size ≥0.20), whilst all other variables displayed no detectable difference (Effect size=<0.20). Table 1 also shows the test-retest reliability of all force variables from the apparatus 100. On the whole absolute force measurements taken during bilateral contractions (ICC ranged from 0.83 to 0.90) were more reliable than the unilateral condition (ICC ranged from 0.56 to 0.80). With respect to between limb imbalances in force, only the bilateral average peak force condition displayed acceptable reliability (ICC=0.84, 95% CI=0.72-0.91).

TABLE 1

Descriptive statistics and test-retest reliability data for variables derived from the apparatus 100 (N = 30)

|  | Test 1 Mean ± SD (N) | Test 2 Mean ± SD (N) | Effect Size (95% CI) | ICC (95% CI) | SWC (N) | TE (N) (95% CI) | % TE (95% CI) |
|---|---|---|---|---|---|---|---|
| | | | Bilateral peak force | | | | |
| Left Leg | 366.4 ± 67.7 | 374.1 ± 60.5 | −0.10 | 0.83 (0.67 to 0.91) | 12.82 | 27.47 (21.87 to 36.92) | 8.53 (6.74 to 11.63) |
| Right Leg | 378.4 ± 68.4 | 391.6 ± 67.0 | −0.20 | 0.90 (0.81 to 0.95) | 13.54 | 21.73 (17.30 to 29.21) | 5.83 (4.62 to 7.92) |
| Imbalance (left:right)* | 0.97 ± 0.11 | 0.96 ± 0.12 | 0.19 | 0.72 (0.49 to 0.86) | 0.02 | 0.06 (0.05 to 0.08) | 6.05 (4.79 to 8.21) |
| | | | Unilateral peak force | | | | |
| Left Leg | 351.3 ± 55.5 | 356.8 ± 65.6 | −0.07 | 0.73 (0.51 to 0.86) | 12.11 | 32.33 (25.74 to 43.46) | 10.23 (8.07 to 13.99) |
| Right Leg | 380.9 ± 60.4 | 370.4 ± 54.7 | 0.09 | 0.56 (0.26 to 0.76) | 11.52 | 38.75 (30.86 to 52.10) | 10.99 (8.66 to 15.05) |
| Imbalance (left:right)* | 0.93 ± 0.11 | 0.96 ± 0.12 | −0.16 | 0.47 (0.13 to 0.70) | 0.02 | 0.09 (0.07 to 0.11) | 10.13 (7.99 to 13.85) |

TABLE 1-continued

Descriptive statistics and test-retest reliability data for variables derived from the apparatus 100 (N = 30)

| | Test 1 Mean ± SD (N) | Test 2 Mean ± SD (N) | Effect Size | ICC (95% CI) | SWC (N) | TE (N) (95% CI) | % TE (95% CI) |
|---|---|---|---|---|---|---|---|
| Bilateral average peak force | | | | | | | |
| Left Leg | 336.3 ± 63.8 | 344.7 ± 61.1 | −0.09 | 0.85 (0.71 to 0.93) | 12.54 | 24.70 (19.67 to 33.21) | 8.40 (6.63 to 11.45) |
| Right Leg | 349.4 ± 64.8 | 361.2 ± 65.1 | −0.16 | 0.89 (0.78 to 0.95) | 12.88 | 22.12 (17.61 to 29.73) | 6.49 (5.14 to 8.82) |
| Imbalance (left:right)* | 0.97 ± 0.10 | 0.96 ± 0.11 | 0.13 | 0.84 (0.72 to 0.91) | 0.02 | 0.04 (0.04 to 0.06) | 4.45 (3.73 to 5.89) |
| Unilateral average peak force | | | | | | | |
| Left Leg | 321.4 ± 54.0 | 323.6 ± 64.2 | 0.01 | 0.79 (0.61 to 0.90) | 11.91 | 27.63 (22.01 to 37.15) | 9.51 (7.51 to 12.99) |
| Right Leg | 341.8 ± 50.9 | 335.8 ± 54.7 | 0.11 | 0.80 (0.63 to 0.90) | 10.62 | 24.14 (19.22 to 32.45) | 7.88 (6.23 to 10.74) |
| Imbalance (left:right)* | 0.94 ± 0.11 | 0.97 ± 0.13 | −0.08 | 0.58 (0.28 to 0.77) | 0.02 | 0.08 (0.06 to 0.10) | 8.72 (6.88 to 11.89) |

*Imbalance data expressed as a ratio and not in Newtons.
Peak force is the highest maximal force recorded from six contractions.
Average peak force is the mean of maximal force recorded from six contractions.
SD, standard deviation; 95% CI, 95% confidence interval;
N, Newtons;
ICC, intraclass correlation coefficient;
SWC, smallest worthwhile change;
TE, total error.

Correlations of the apparatus 100 force, data to the reciprocal torque measurements derived from the isokinetic dynamometer can be found in Tables 2 and 3. On both limbs, forces measured with the apparatus 100 during bilateral contractions correlated significantly (p<0.05) with the corresponding dynamometry derived torque collected during unilateral contraction at both speeds (r values ranged from 0.39 to 0.58). With respect to unilateral forces from the apparatus 100 only right limb data correlated significantly (p<0.01) with dynamometry torques at both speeds (r value ranged from 0.57 to 0.63), whilst left limb forces showed no such correlation at any speeds (r values ranged from 0.29 to 0.35). With reference to between limb imbalances only unilateral average peak force imbalance (LL:RL) correlated with between limb torque imbalances (LL:RL) measured at $-120°·s^{-1}$ (r value=0.43).

TABLE 2

Correlation data comparing bilateral and unilateral force data from the apparatus 100 to unilateral dynamometry data at two isokinetic velocities (N = 29)

| | | LL Bilateral Avg Peak Force | LL Bilateral Peak Force | LL Unilateral Avg Peak Force | LL Bilateral Peak Force | RL Bilateral Avg Peak Force | RL Bilateral Peak Force | RL Unilateral Avg Peak Force | RL Unilateral Peak Force |
|---|---|---|---|---|---|---|---|---|---|
| LL Torque 30°·s−1 | Pearson correlation | 0.387* | 0.422* | 0.289 | 0.291 | | | | |
| | Sig. (2-tailed) | 0.038 | 0.022 | 0.128 | 0.126 | | | | |
| | N | 29 | 29 | 29 | 29 | | | | |
| LL Torque 120°·s−1 | Pearson correlation | 0.386* | 0.390* | 0.291 | 0.345 | | | | |
| | Sig. (2-tailed) | 0.039 | 0.036 | 0.125 | 0.067 | | | | |
| | N | 29 | 29 | 29 | 29 | | | | |
| RL Torque 30°·s−1 | Pearson correlation | | | | | 0.528** | 0.518** | 0.629** | 0.602** |
| | Sig. (2-tailed) | | | | | 0.003 | 0.004 | 0.000 | 0.001 |
| | N | | | | | 29 | 29 | 29 | 29 |

TABLE 2-continued

Correlation data comparing bilateral and unilateral force data from the apparatus 100 to unilateral dynamometry data at two isokinetic velocities (N = 29)

|  |  | LL Bilateral Avg Peak Force | LL Bilateral Peak Force | LL Unilateral Avg Peak Force | LL Bilateral Peak Force | RL Bilateral Avg Peak Force | RL Bilateral Peak Force | RL Unilateral Avg Peak Force | RL Unilateral Peak Force |
|---|---|---|---|---|---|---|---|---|---|
| RL Torque 120°·s−1 | Pearson correlation |  |  |  |  | 0.556** | 0.582** | 0.568** | 0.578** |
|  | Sig. (2-tailed) |  |  |  |  | 0.002 | 0.001 | 0.001 | 0.001 |
|  | N |  |  |  |  | 29 | 29 | 29 | 29 |

Correlations denoted as significant at *p < 0.05 or **p < 0.01.
LL, left limb;
RL, right limb.
Peak force is the highest maximal force recorded from six contractions. Average peak force is the mean of maximal force recorded from six contractions.

TABLE 3

Correlation data comparing bilateral and unilateral force data from the apparatus 100 to unilateral dynamometry data at two isokinetic velocities (N = 29)

|  |  | Imbalance (LL:RL) Bilateral Avg | Imbalance (LL:RL) Bilateral Peak | Imbalance (LL:RL) Unilateral Avg | Imbalance (LL:RL) Unilateral Peak |
|---|---|---|---|---|---|
| Torque Imbalance (LL:RL) 30°·s−1 | Pearson correlation | −0.028 | −0.038 | 0.260 | 0.122 |
|  | Sig. (2-tailed) | 0.885 | 0.846 | 0.173 | 0.530 |
|  | N | 29 | 29 | 29 | 29 |
| Torque Imbalance (LL:RL) 120°·s−1 | Pearson correlation | 0.230 | 0.155 | 0.426* | 0.365 |
|  | Sig. (2-tailed) | 0.239 | 0.431 | 0.024 | 0.056 |
|  | N | 29 | 29 | 29 | 29 |

Correlations denoted as significant at *p <0.05. LL, left limb; RL, right limb. Peak force is the highest maximal force recorded from six contractions. Average peak force is the mean of maximal force recorded from six contractions. Imbalance determined from the quotient of left limb and right limb forces from the apparatus 100, or left limb and right limb torque from the isokinetic dynamometer. Peak force is the highest maximal force recorded from six contractions on each limb. Average peak force is the mean of maximal force recorded from six contractions on each limb.

From the data presented, the apparatus 100 displays acceptable levels of test-retest reliability when measuring peak or average peak knee flexor force during a bilateral NHE and approaches an acceptable level of reliability for average peak force during unilateral contractions. For the measurement of between limb strength differences, only when the NHE was completed bilaterally, and peak force was average across six contractions, did the measure display acceptable reliability. Hence, the findings from the current study suggests that the single most reliable method to acquire eccentric knee flexor force and between limb force ratios from the apparatus 100 is via a bilateral NHE with peak force averaged across six contractions. There is also the capability to assess eccentric knee flexor strength during a bilateral contraction but using a single peak measure instead of an average of peak forces, or during unilateral contraction, however the between limb strength comparisons, and in some cases the absolute force measures, do not appear to be reliable for these methods. Therefore, it appears that a bilateral NHE performed with multiple repetitions across a number of sets to determine average eccentric peak knee flexor force produces optimal reliability. For the purposes of maximal strength assessment it is important to minimise the number of repetitions per set to reduce the impact of fatigue throughout a set because this will have a significant impact on average peak force. In the current study two sets of three repetitions were performed, but similar set and repetition formats (i.e. three sets of two repetitions) are also feasible. It is also recommend that measures of eccentric knee flexor strength and between limb strength imbalances be used to compare within but not between athletes. This is due to the varying factors which influence the performance of the NHE, such as lever lengths and upper body mass that would differ markedly between athletes, but would be expected to remain mostly similar within an athlete.

With respect to concurrent validity, bilateral NHE forces for both limbs correlated significantly with unilateral isokinetic eccentric knee flexor torque, whilst correlations between unilateral NHE forces and unilateral isokinetic eccentric knee flexor torque were mixed perhaps owing to the larger amount of variability within unilateral contractions. When comparing between limb strength differences only one correlation was detected from eight comparisons (dynamometer torque imbalance (LL:RL) at $120°.s^{-1}$ vs. Nordic unilateral average peak force imbalance (LL:RL)). This would suggest that, on the whole, the findings of between limb strength imbalance from the apparatus 100 are not relatable to reciprocal measure derived from the isokinetic dynamometer.

The correlation analysis suggests that to some extent the two devices are measuring similar strength qualities within participants. However, whilst significant, the reported r values suggest that the relationship between the two modalities is moderate at best (significant r values range from 0.39 to 0.63). The variance in strength measures between the two devices may be explained by the inherent differences between the two movement patterns required. The apparatus 100 measures force in a variable speed movement, requiring the hamstrings to act around the knee joint to control the descent of the upper body but also across the hip to maintain the upper body in a neutral position and can be performed bilaterally or unilaterally. Knee flexor strength assessment on an isokinetic dynamometer is a constant movement speed torque measurement, isolated to the knee joint and can only be performed unilaterally. It is feasible to suggest that differences in movement speed shouldn't have a great influence over maximal eccentric force generation, as per the force-velocity relationship. Despite this the differences in the movement pattern would be expected to influence the strength quality that is measured and would, to some extent, explain the variance seen between the testing modalities. It might also be expected that the difference in laterality between the bilateral NHE and the unilateral dynamometry testing would contribute to some of the variability, however on the whole, the unilateral NHE displayed weaker correlations than the bilateral contractions. This may be due in part to the difficulty participants experienced in becoming comfortable with the unilateral condition, as exemplified by the greater amount of familiarisation time that was required to be devoted to the unilateral contractions.

Aside from the bilateral NHE condition displaying the highest level of test-retest reliability, the ability to assess unilateral eccentric knee flexor strength during bilateral contractions may have additional benefits. It is well known that there are complexities in the neural control of bilateral and unilateral contractions, with the bilateral deficit a primary example of such a phenomenon. It would appear feasible that under bilateral conditions, in a task with a known but ever increasing load such as the NHE, the nervous system may elect to protect a weaker or more vulnerable muscle/limb and consequently chose to 'load' the more capable muscle or limb more aggressively. As such bilateral testing may be better able to detect between limb strength imbalances, if they exist, compared with unilateral strength assessments which have already shown some predictive ability. This is particularly pertinent for the monitoring of HSI risk in athletes, given between limb strength difference have been reported to increase the risk of injury in athletes. Indeed, unpublished observations show that in elite athletes with a previous unilateral HSI history, the apparatus 100 has been able to better predict the previously injured limb compared to the isokinetic dynamometer, based on between limb eccentric strength deficits.

Intervention Experiment

Four recreationally active males participated in 10 training sessions over a four week period. Participants performed six sets of eight repetitions of eccentric knee flexor isokinetic exercise for the left limb, whilst the right limb remain untrained and served as the control limb. Prior to, and following the completion of the intervention, participants had their level of eccentric knee flexor strength measured using the apparatus 100 by performing two sets of two bilateral Nordic hamstring exercises. One-tailed paired t-tests were used to compare eccentric knee flexor strength of both legs (pre vs post).

Results: The left (trained) limb showed a significant increase in eccentric knee flexor strength (pre=370.38N±76.17N; post=391.64±73.85; mean difference=21.26N, p=0.009) whilst the right (control) limb displayed no change (pre=390.57N±51.74; post=383.12N±47.76N; mean difference=−7.45N, p=0.190).

Accordingly, the apparatus 100 can reliably detect improvements in hamstring strength over a period of training.

Injured Cross-Sectional Experiments

Four active males with a clinically diagnosed unilateral hamstring strain injury were recruited to participate in the current study. All athletes performed two sets of two bilateral Nordic hamstring exercises on the apparatus 100 to determine eccentric knee flexor strength for both the previously injured and uninjured limb. One-tailed paired t-tests were used to compare eccentric knee flexor strength between limbs.

Results: The previously injured limb (385.22N±14.19N) was significantly (p=0.041) weaker than the uninjured limb (425.30N±26.40).

The above experiments exclude normalisation, for example for subject height, weight, population statistics, or the like. However, it will be appreciated that normalisation could be performed, either in the processing system 1100, or in a separate electronic processing device, such that indicators are baselined according a reference population, for example, by aggregate population, or demographically segregated.

In view of these experiments, it will be appreciated that the apparatus 100 is capable of effectively assessing the hamstring strength of a subject S, and in particular displays acceptable levels of test-retest reliability and correlation with gold standard, i.e. isokinetic dynamometry, assessments. Furthermore, the apparatus 100 displays promising results in intervention and cross-sectional injury investigations.

It will be appreciated that an apparatus 100 with the above described examples, facilitates a simplified method for assessing hamstring strength of a subject. For example, in contrast to the current gold standard in hamstring strength assessment, i.e. isokinetic dynamometry, the apparatus 100 provides for a reduction in manufacturing costs, increased portability, decreased assessment times, and does not require supervision by highly trained personnel.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described. Thug, for example, it will be appreciated that features from different examples above may be used interchangeably where appropriate.

The claims defining the invention are as follows:

1. An apparatus comprising:
   a support having an engagement area configured to receive a first knee of a first leg of a subject and a second knee of a second leg of the subject while the subject is engaged in a kneeling position;
   a first leg restraint mounted to the support via a first pivotal mount, and wherein the first leg restraint is configured to secure a first ankle of the subject relative to the support while the subject is engaged in the kneeling position and thereby secure the first knee of the subject to a first portion of the support while the subject performs an eccentric contraction of at least a hamstring muscle of the first leg;

a second leg restraint mounted to the support via a second pivotal mount, and wherein the second leg restraint is configured to secure a second ankle of the subject relative to the support while the subject is engaged in the kneeling position and thereby secure the second knee of the subject to a second portion of the support while the subject performs an eccentric contraction of at least a hamstring muscle of the second leg;

a first force sensor coupled to the first leg restraint by the first pivotal mount and configured to sense a first force applied to the first leg restraint and generate a first output signal;

a second force sensor coupled to the second leg restraint by the second pivotal mount and configured to sense a second force applied to the second leg restraint and generate a second output signal; and an electronic processing device configured for:
   monitoring the first output signal and the second output signal;
   generating, based on the first output signal, a first indicator of a strength of a first knee flexor muscle of the subject while the subject performs the eccentric contraction of the at least the hamstring muscle of the first leg; and
   generating, based on the second output signal, a second indicator of a strength of a second knee flexor muscle of the subject while the subject performs the eccentric contraction of the at least the hamstring muscle of the second leg.

2. The apparatus of claim 1, wherein said engagement area is one portion of the support and said first leg restraint and said second leg restraint are arranged on another portion of the support, said support being configured so that said engagement area is operatively higher than said another portion.

3. The apparatus of claim 1, wherein said engagement area is at least one knee support configured in a stepped arrangement relative to a remainder of said support.

4. The apparatus of claim 3, wherein said at least one knee support is operatively higher than said remainder of said support.

5. The apparatus of claim 3, wherein said at least one knee support is movable relative to said remainder of said support.

6. The apparatus of claim 3, wherein the at least one knee support is composed of foam.

7. The apparatus of claim 1, wherein said first leg restraint and said second leg restraint are moveable relative to each other.

8. The apparatus of claim 1, wherein said first leg restraint is detachable from the first pivotal mount, and said second leg restraint is detachable from the second pivotal mount.

9. The apparatus of claim 8, wherein said first pivotal mount and said second pivotal mount are each detachable from said support.

10. The apparatus of claim 1, wherein each of the first and second leg restraints is a C-shaped member.

11. The apparatus of claim 10, wherein each C-shaped member is attached to said support with said sensors interposed between respective C-shaped members and said support.

12. The apparatus of claim 1, comprising:
   a first movable coupling configured to allow the first force sensor to pivot relative to the support; and
   a second movable coupling configured to allow the second force sensor to pivot relative to the support.

13. The apparatus of claim 1, wherein the electronic processing device is further configured for:
   comparing the first output signal with reference data to generate the first indicator; and
   comparing the second output signal with reference data to generate the second indicator.

14. The apparatus of claim 1, wherein the first pivotal mount and second pivotal mount each comprise a ball and socket joint.

* * * * *